(12) United States Patent
Jagasia et al.

(10) Patent No.: US 9,464,049 B2
(45) Date of Patent: Oct. 11, 2016

(54) INDOLE-CARBOXAMIDES

(71) Applicant: Hoffmann-La Roche Inc., Little Falls, NJ (US)

(72) Inventors: Ravi Jagasia, Loerrach (DE); Roland Jakob-Roetne, Inzlingen (DE); Jens-Uwe Peters, Grenzach-Wyhlen (DE); Juergen Wichmann, Steinen (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 15/066,154

(22) Filed: Mar. 10, 2016

(65) Prior Publication Data
US 2016/0185721 A1  Jun. 30, 2016

Related U.S. Application Data

(63) Continuation of application No. PCT/EP2014/069235, filed on Sep. 10, 2014.

(30) Foreign Application Priority Data

Sep. 12, 2013  (EP) .................................. 13184157

(51) Int. Cl.
- *C07D 209/42* (2006.01)
- *C07D 209/30* (2006.01)
- *A61K 31/4045* (2006.01)
- *C07D 401/04* (2006.01)

(52) U.S. Cl.
CPC ......... *C07D 209/42* (2013.01); *A61K 31/4045* (2013.01); *C07D 209/30* (2013.01); *C07D 401/04* (2013.01)

(58) Field of Classification Search
None
See application file for complete search history.

(56) References Cited

U.S. PATENT DOCUMENTS 7,838,542 B2 * 11/2010 Hangauer, Jr. ....... C07D 209/42
                                                            514/359

FOREIGN PATENT DOCUMENTS

| WO | 2008/002674 A2 | 1/2008 |
| WO | 2012/006419 A2 | 1/2012 |
| WO | 2014/023674 A1 | 2/2014 |

OTHER PUBLICATIONS

Database CAPLUS in STN, Hangauer, U.S. Pat. No. 7,838,542 B2 (Nov. 23, 2010) (abstract).*
Bielefield et al., "Protection from impulse noise-induced hearing loss with novel Src-protein tyrosine kinase inhibitors", Neuroscience Research 71(4):348-354 (Jul. 29, 2011).
MacMillan, "Development of Proneurogenic, Neuroprotective Small Molecules" J. Am. Chem. Soc. 133:1428-1437 (2011).
Pieper et al., "P7C3 and an unbiased approach to drug discovery for neurodegenerative disease" Chem Soc Rev 43:6716 (2014).

* cited by examiner

*Primary Examiner* — Brian J Davis

(57) ABSTRACT

The present invention relates to compounds of general formula

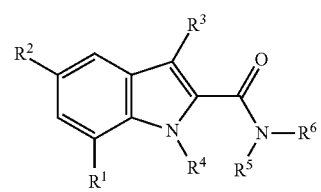

wherein $R^1$, $R^2$, $R^3$, $R^4$, $R^5$ and $R^6$ are as defined herein are useful for the treat of neurological and neuropsychiatric conditions.

11 Claims, No Drawings

INDOLE-CARBOXAMIDES

CROSS REFERENCE TO RELATED APPLICATIONS

This application is a continuation of International Application No. PCT/EP2014/069235 having an international filing date of Jul. 28, 2014 and which claims benefit under 35 U.S.C. §119 to European Patent Application No. 13184157.90 filed Sep. 12, 2013. The entire contents of both are incorporated herein by reference.

FIELD OF THE INVENTION

The present invention relates to novel compounds of formula I, wherein $R^1$, $R^2$, $R^3$, $R^4$, $R^5$ and $R^6$ are as described herein, having pharmaceutical activity, their manufacture, pharmaceutical compositions containing them and their potential use as medicaments.

BACKGROUND OF THE INVENTION

Neurogenesis occurs in the developing and adult brain. Conceptually, the process of neurogenesis can be divided into four steps: (i) proliferation of neural stem cells (NSCs); (ii) neuronal fate determination of NSC; (iii) survival and maturation of new neurons; and (iv) functional integration of new neurons into the neuronal network.

Adult neurogenesis is a developmental process that occurs throughout live in the adult brain whereby new functional neurons are generated from adult neural stem cells. Constitutive adult neurogenesis under physiological conditions occurs mainly in two "neurogenic" brain regions, 1) the sub-granular zone (SGZ) in the dentate gyms of the hippocampus, where new dentate granule cells are generated, 2) the sub-ventricular zone (SVZ) of the lateral ventricles, where new neurons are generated and then migrate through the rostral migratory stream (RMS) to the olfactory bulb to become interneurons.

Extensive evidence suggests that hippocampal adult neurogenesis plays an important role in cognitive and emotional states albeit the precise function remains elusive. It has been argued that the relatively small number of newborn granule neurons can affect global brain function because they innervate many interneurons within the dentate gyms, each of which inhibits hundreds of mature granule cells leading to a neurogenesis-dependent feedback inhibition. In combination with a low threshold for firing the newborn neurons trigger responses to very subtle changes in context. Disturbances in this process may manifest behaviorally in deficits in pattern separation related to psychiatric diseases. For example, adult hippocampal neurogenesis correlates with cognitive and emotional capacity, e.g. physical exercise, exposure to an enriched environment and typical antidepressants concomitantly promote adult hippocampal neurogenesis and cognition and/or emotional states, while chronic stress, depression, sleep deprivation and aging decrease adult neurogenesis and associate with negative cognitive and/or emotional states (Neuron 70, May 26, 2011, pp 582-588 and pp 687-702; WO 2008/046072). Interestingly, antidepressants promote hippocampal adult neurogenesis and their effects on certain behaviors require the stimulation of neurogenesis. Neurogenesis in other adult CNS regions is generally believed to be very limited under normal physiological conditions, but could be induced after injury such as stroke, and central and peripheral brain damage.

It is therefore believed that stimulation of adult neurogenesis represents a neuro-regenerative therapeutic target for normal aging and in particular for a variety of neurodegenerative and neuropsychiatric diseases, including schizophrenia, obsessive-compulsive personality disorder, major depression, bipolar disorders, anxiety disorders, epilepsy, retinal degeneration, traumatic brain injury, spinal cord injury, post-traumatic stress disorder, panic disorder, Parkinson's disease, dementia, Alzheimer's disease, mild cognitive impairment, chemotherapy-induced cognitive dysfunction ("chemobrain"), Down syndrome, autism spectrum disorders, hearing loss (Neuroscience, 167 (2010) 1216-1226; Nature Medicine, Vol. 11, number 3, (2005), 271-276) tinnitus, spinocerebellar ataxia, amyotrophic lateral sclerosis, multiple sclerosis, Huntington's disease, stroke, and disturbances due to radiation therapy, chronic stress, or abuse of neuro-active drugs, such as alcohol, opiates, methamphetamine, phencyclidine and cocaine (US 2012/0022096).

Hence, chemical stimulation of adult neurogenesis offers new regenerative avenues and opportunities to develop novel drugs for treating neurological diseases and neuropsychiatric disorders.

Compounds that modulate neurogenesis may therefore useful for treating of schizophrenia, obsessive-compulsive personality disorder, major depression, bipolar disorders, anxiety disorders, normal aging, epilepsy, retinal degeneration, traumatic brain injury, spinal cord injury, post-traumatic stress disorder, panic disorder, Parkinson's disease, dementia, Alzheimer's disease, cognitive impairment, chemotherapy-induced cognitive dysfunction ("chemobrain"), Down syndrome, autism spectrum disorders, hearing loss, tinnitus, spinocerebellar ataxia, amyotrophic lateral sclerosis, multiple sclerosis, Huntington's disease, stroke, and disturbances due to radiation therapy, chronic stress, optic neuropathy or macular degeneration, or abuse of neuro-active drugs, such as alcohol, opiates, methamphetamine, phencyclidine and cocaine.

The most preferred indications for compounds of formula I are Alzheimer's disease, depression, anxiety disorders and stroke.

BRIEF SUMMARY OF THE INVENTION

The present invention relates to compounds of general formula

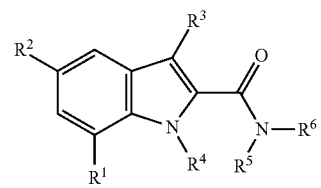

wherein
$R^1$ is aryl or heteroaryl, which are optionally substituted by one, two or three substituents, selected from lower alkyl, halogen, lower alkyl substituted by halogen, hydroxyl, lower alkoxy, lower alkoxy substituted by halogen, cyano or nitro;
$R^2$ is halogen, lower alkyl or cyano;
$R^3$ is hydrogen or lower alkyl;
$R^4$ is hydrogen or lower alkyl;

$R^5$, $R^6$ are hydrogen, lower alkyl, or may form together with the N-atom to which they are attached a heterocycloalkyl ring;

or to a pharmaceutically acceptable acid addition salt, to a racemic mixture or to its corresponding enantiomer and/or optical isomers thereof.

The present invention further relates to a method for the treatment of schizophrenia, obsessive-compulsive personality disorder, major depression, bipolar disorders, anxiety disorders, normal aging, epilepsy, retinal degeneration, traumatic brain injury, spinal cord injury, post-traumatic stress disorder, panic disorder, Parkinson's disease, dementia, Alzheimer's disease, cognitive impairment, chemotherapy-induced cognitive dysfunction, Down syndrome, autism spectrum disorders, hearing loss, tinnitus, spinocerebellar ataxia, amyotrophic lateral sclerosis, multiple sclerosis, Huntington's disease, stroke, radiation therapy, chronic stress, optic neuropathy or macular degeneration, abuse of neuro-active drugs, such as alcohol, opiates, methamphetamine, phencyclidine and cocaine, which method comprises administering an effective amount of a compound of formula I.

DETAILED DESCRIPTION OF THE INVENTION

One embodiment of the invention is compounds of formula 1 and pharmaceutical compositions, containing a compound of formula I.

One further object of the present invention is the use of a compound of formula I for the preparation of medicaments for the therapeutic and/or prophylactic treatment of the above-mentioned diseases.

A further object of the invention is a method for the treatment of schizophrenia, obsessive-compulsive personality disorder, major depression, bipolar disorders, anxiety disorders, normal aging, epilepsy, retinal degeneration, traumatic brain injury, spinal cord injury, post-traumatic stress disorder, panic disorder, Parkinson's disease, dementia, Alzheimer's disease, cognitive impairment, chemotherapy-induced cognitive dysfunction, Down syndrome, autism spectrum disorders, hearing loss, tinnitus, spinocerebellar ataxia, amyotrophic lateral sclerosis, multiple sclerosis, Huntington's disease, stroke, radiation therapy, chronic stress, abuse of neuro-active drugs, such as alcohol, opiates, methamphetamine, phencyclidine and cocaine, which method comprises administering an effective amount of a compound of formula I.

One embodiment of the invention are compounds of formula I, wherein $R^1$ is aryl, for example phenyl, which is optionally substituted by one, two or three substituents, selected from lower alkyl, halogen, lower alkyl substituted by halogen, hydroxyl, lower alkoxy, lower alkoxy substituted by halogen, cyano or nitro, for example the following compounds 7-(4-chlorophenyl)-5-cyano-1,3-dimethylindole-2-carboxamide
5-fluoro-7-(4-fluorophenyl)-1-methylindole-2-carboxamide
5-fluoro-7-(4-fluorophenyl)-1H-indole-2-carboxamide
5-cyano-7-(4-fluorophenyl)-1,3-dimethylindole-2-carboxamide
5-cyano-7-(3,4-difluorophenyl)-1,3-dimethylindole-2-carboxamide
5-cyano-1,3-dimethyl-7-[4-(trifluoromethyl)-phenyl]-indole-2-carboxamide
5-cyano-7-(3,4-difluorophenyl)-3-methyl-1H-indole-2-carboxamide
5-Cyano-3-methyl-7-[4-(trifluoromethyl)phenyl]-1H-indole-2-carboxamide
5-cyano-7-(4-fluorophenyl)-3-methyl-1H-indole-2-carboxamide
7-(4-chlorophenyl)-5-cyano-3-methyl-1H-indole-2-carboxamide
5-chloro-7-(4-fluorophenyl)-3-methyl-1H-indole-2-carboxamide
5-chloro-7-(4-chlorophenyl)-3-methyl-1H-indole-2-carboxamide
5-chloro-7-(4-fluorophenyl)-1,3-dimethylindole-2-carboxamide
5-chloro-7-(4-chlorophenyl)-1,3-dimethylindole-2-carboxamide
5-chloro-7-(3,4-difluorophenyl)-3-methyl-1H-indole-2-carboxamide
5-chloro-3-methyl-7-[4-(trifluoromethyl)-phenyl]-1H-indole-2-carboxamide
5-chloro-7-(3,4-difluorophenyl)-1,3-dimethylindole-2-carboxamide
5-chloro-1,3-dimethyl-7-[4-(trifluoromethyl)phenyl]indole-2-carboxamide
5-cyano-3-methyl-7-[4-(trifluoromethoxy)-phenyl]-1H-indole-2-carboxamide
5-cyano-7-(4-cyanophenyl)-3-methyl-1H-indole-2-carboxamide
5-cyano-1,3-dimethyl-7-[4-(trifluoromethoxy)phenyl]indole-2-carboxamide
5-cyano-7-(4-cyanophenyl)-1,3-dimethylindole-2-carboxamide
5-chloro-7-(4-cyanophenyl)-3-methyl-1H-indole-2-carboxamide
5-chloro-3-methyl-7-[4-(trifluoromethoxy)phenyl]-1H-indole-2-carboxamide
5-chloro-7-(2,4-difluorophenyl)-3-methyl-1H-indole-2-carboxamide
5-chloro-7-(2,4-dichlorophenyl)-3-methyl-1H-indole-2-carboxamide
5-chloro-1,3-dimethyl-7-[4-(trifluoromethoxy)-phenyl]indole-2-carboxamide
5-chloro-7-(4-cyanophenyl)-1,3-dimethylindole-2-carboxamide
5-chloro-7-(2,4-difluorophenyl)-1,3-dimethylindole-2-carboxamide
5-chloro-7-(2,4-dichlorophenyl)-1,3-dimethylindole-2-carboxamide
5-chloro-7-(4-chloro-3-fluorophenyl)-3-methyl-1H-indole-2-carboxamide
5-chloro-7-(4-chloro-3-fluorophenyl)-1,3-dimethylindole-2-carboxamide
5-cyano-7-(3,4-difluorophenyl)-1H-indole-2-carboxamide
5-cyano-7-(4-fluorophenyl)-1H-indole-2-carboxamide
7-(4-chlorophenyl)-5-cyano-1H-indole-2-carboxamide
5-cyano-7-[4-(trifluoromethyl)phenyl]-1H-indole-2-carboxamide
5-cyano-1-methyl-7-[4-(trifluoromethyl)-phenyl]-indole-2-carboxamide
5-cyano-7-(4-fluorophenyl)-1-methylindole-2-carboxamide
7-(4-chlorophenyl)-5-cyano-1-methylindole-2-carboxamide
5-cyano-7-(3,4-difluorophenyl)-1-methylindole-2-carboxamide
5-cyano-7-(2,4-difluorophenyl)-1H-indole-2-carboxamide
5-cyano-7-(2,4-dichlorophenyl)-1H-indole-2-carboxamide
5-cyano-7-(4-cyanophenyl)-1H-indole-2-carboxamide
5-cyano-7-[4-(trifluoromethoxy)-phenyl]-1H-indole-2-carboxamide 5-fluoro-7-(4-fluorophenyl)-3-methyl-1H-indole-2-carboxamide
7-(4-chlorophenyl)-5-fluoro-3-methyl-1H-indole-2-carb oxamide
7-(3,4-difluorophenyl)-5-fluoro-3-methyl-1H-indole-2-carboxamide
5-fluoro-3-methyl-7-[4-(trifluoromethyl)-phenyl]-1H-indole-2-carboxamide
5-fluoro-7-(4-fluorophenyl)-1,3-dimethylindole-2-carboxamide
7-(4-chlorophenyl)-5-fluoro-1,3-dimethylindole-2-carboxamide
5-fluoro-1,3-dimethyl-7-[4-(trifluoromethyl)-phenyl]-indole-2-carb oxamide
7-(3,4-difluorophenyl)-5-fluoro-1,3-dimethylindole-2-carboxamide
7-(4-cyanophenyl)-5-fluoro-3-methyl-1H-indole-2-carboxamide
5-fluoro-3-methyl-7-[4-(trifluoromethoxy)phenyl]-1H-indole-2-carboxamide
7-(2,4-difluorophenyl)-5-fluoro-3-methyl-1H-indole-2-carboxamide
7-(2,4-dichlorophenyl)-5-fluoro-3-methyl-1H-indole-2-carboxamide
7-(4-chloro-2-fluorophenyl)-5-cyano-1H-indole-2-carboxamide
7-(4-chloro-2-fluorophenyl)-5-cyano-1-methylindole-2-carboxamide
7-(4-cyanophenyl)-5-fluoro-1,3-dimethylindole-2-carboxamide
5-fluoro-1,3-dimethyl-7-[4-(trifluoromethoxy)phenyl]indole-2-carb oxamide
7-(2,4-dichlorophenyl)-5-fluoro-1,3-dimethylindole-2-carboxamide
5-cyano-7-(2,4-difluorophenyl)-1-methylindole-2-carboxamide
5-cyano-7-(2,4-dichlorophenyl)-1-methylindole-2-carboxamide
7-(2,4-difluorophenyl)-5-fluoro-1,3-dimethylindole-2-carboxamide
5-cyano-7-(4-fluoro-3-methylphenyl)-1-methylindole-2-carboxamide
5-cyano-7-(4-fluoro-3-methylphenyl)-1H-indole-2-carboxamide
5-cyano-1-methyl-7-(4-nitrophenyl)-indole-2-carboxamide
5-cyano-7-(4-nitrophenyl)-1H-indole-2-carboxamide
5-cyano-7-(4-methoxyphenyl)-1-methylindole-2-carboxamide
5-cyano-7-(4-methoxyphenyl)-1H-indole-2-carboxamide
5-cyano-1-methyl-7-[4-(trifluoromethoxy)phenyl]indole-2-carboxamide
5-fluoro-3-methyl-7-(4-methylphenyl)-1H-indole-2-carb oxamide
5-fluoro-3-methyl-7-(2,3,4-trifluorophenyl)-1H-indole-2-carb oxamide
5-fluoro-7-(4-methoxyphenyl)-3-methyl-1H-indole-2-carboxamide
7-(4-chloro-2-fluorophenyl)-5-fluoro-3-methyl-1H-indole-2-carboxamide
5-fluoro-3-methyl-7-pyridin-4-yl-1H-indole-2-carboxamide.

One embodiment of the invention are further compounds of formula I, wherein R¹ is heteroaryl, for example pyridinyl, which is optionally substituted by one, two or three substituents, selected from lower alkyl, halogen, lower alkyl substituted by halogen, hydroxyl, lower alkoxy, lower alkoxy substituted by halogen, cyano or nitro, for example the following compounds
7-(2-chloropyridin-4-yl)-5-cyano-1-methylindole-2-carb oxamide
7-(2-chloropyridin-4-yl)-5-cyano-1H-indole-2-carboxamide
5-fluoro-3-methyl-7-pyridin-4-yl-1H-indole-2-carboxamide.

The following definitions of the general terms used in the present description apply irrespective of whether the terms in question appear alone or in combination.

As used herein, the term "aryl" denotes a carbocyclic ring system, containing from 6 to 10 carbon atoms forming one or more rings, and wherein at least one ring is aromatic in nature, for example phenyl or naphthyl. The most preferred aryl group is phenyl.

The term "heteroaryl" denotes a carbocyclic ring system, containing from 5 to 10 ring atoms forming one or more rings, wherein at least one carbon atom is replaced by a heteroatom, selected from the group consisting of O, N or S, and wherein at least one ring is aromatic in nature, for example oxazolyl, pyridyl, thiophenyl, quinolinyl, pyrrolyl, furyl, benzoimidazolyl, imidazolyl and the like. The most preferred group is pyridyl.

The term "lower alkyl" denotes a saturated, i.e. aliphatic hydrocarbon group including a straight or branched carbon chain with 1-4 carbon atoms. Examples for "alkyl" are methyl, ethyl, n-propyl and isopropyl.

The term "alkoxy" denotes a group —O—R' wherein R' is lower alkyl as defined above.

The term "lower alkyl substituted by halogen" denotes a lower alkyl group as defined above, wherein at least one hydrogen atom is replaced by a halogen atom. The preferred group is $CF_3$.

The term "lower alkoxy substituted by halogen" denotes a lower alkoxy group as defined above, wherein at least one hydrogen atom is replaced by a halogen atom. The preferred group is $OCF_3$.

The term "halogen" denotes chlorine, bromine, fluorine or iodine.

The term "heterocycloalkyl" denotes an unsaturated carbon ring, wherein one or two carbon atoms are replaced by N, O or S, for example piperidinyl, morpholinyl, piperazinyl, pyrrolidinyl.

The term "pharmaceutically acceptable salt" or "pharmaceutically acceptable acid addition salt" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

The present new compounds of formula I and their pharmaceutically acceptable salts can be prepared by methods known in the art, for example, by processes described below, which process comprises a) reacting a compound of formula II wherein X is halo or —OH

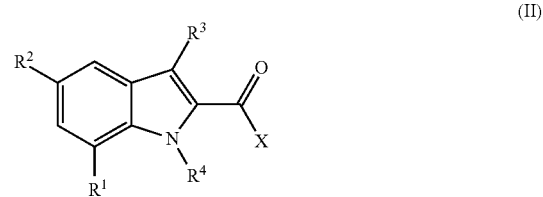

with a compound of formula III $$NHR^5R^6 \quad (III)$$

to afford a compound of formula I

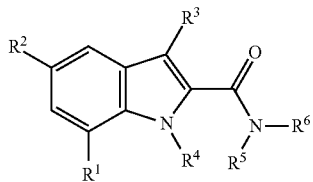

and, if desired, converting the compounds obtained into pharmaceutically acceptable acid addition salts, or
  a) reacting a compound of formula IV

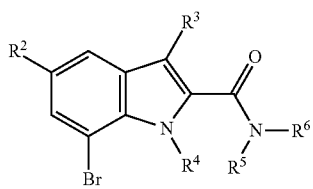

with a compound of formula V

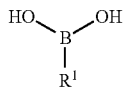

to afford a compound of formula I

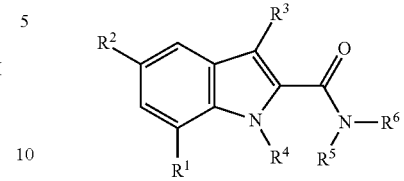

and, if desired, converting the compounds obtained into pharmaceutically acceptable acid addition salts.

The preparation of compounds of formula I of the present invention may be carried out in sequential or convergent synthetic routes. Syntheses of the compounds of the invention are shown in the following scheme 1. The skills required for carrying out the reaction and purification of the resulting products are known to those skilled in the art. The substituents and indices used in the following description of the processes have the significance given herein before unless indicated to the contrary.

In more detail, the compounds of formula I can be manufactured by the methods given below, by the methods given in the examples or by analogous methods. Appropriate reaction conditions for the individual reaction steps are known to a person skilled in the art. The reaction sequence is not limited to the one displayed in scheme 1, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

Scheme 1

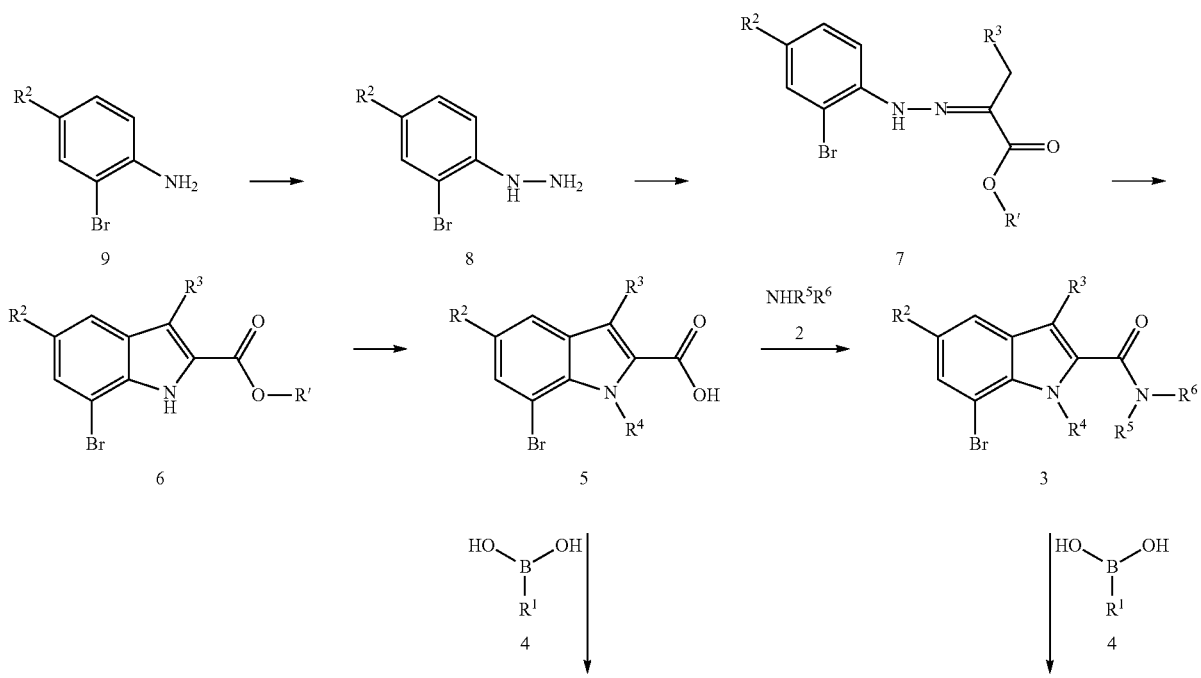

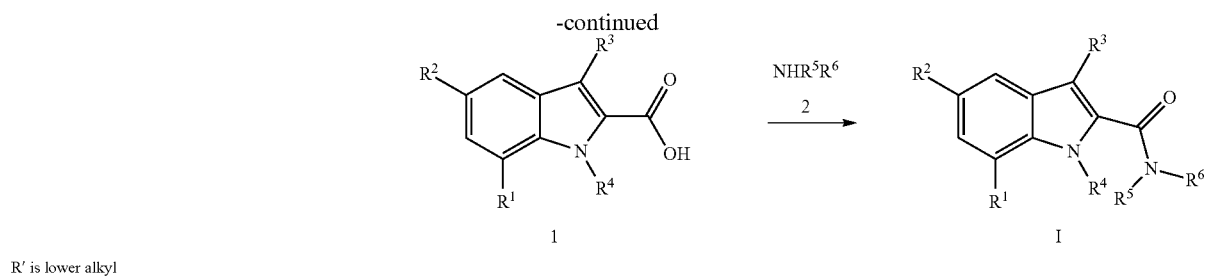

R' is lower alkyl

Starting from the anilines of formula 9, the corresponding hydrazines of formula 8 were prepared. These derivatives were the starting points for the classical indole synthesis yielding the indole-2-carboxylates of formula 6 via the intermediates of formula 7.

Amides (3 and I) may be formed from the corresponding esters or carboxylic acids by methods well known in the art. Esters can be hydrolyzed to a carboxylic acid (5) which is converted to an acid chloride and treated with ammonium hydroxide or an appropriate amine. Alternatively the carboxylic acid may be activated with well-known peptide coupling reagents such as 1-[3-(dimethylamino)propyl]-3-ethylcarbodiimide hydrochloride (ECDI), 1,1'-carbonyidi-imidazole (CDI) or 1,3-dicyclohexylcarbodiimide (DCC) optionally with HOAT (1-hydroxy-7-azabenzotriazole) or HOBT (1-hydroxybenzotriazole hydrate) subsequently and reacted with an appropriate amine in the presence of a base.

Suzuki coupling of commercially available boronic acids with 3 also affords the final compounds of formula I. The Suzuki reaction (N. Miyama and A. Suzuki, *Chem Rev.* 1995 95:2457-2483; A. Suzuki, *J. Organometallic Chem* 1999 576:147-168) is a palladium-catalyzed coupling reaction well-known in the art which can be utilized in bond formation to biaryl compounds. The amide formation and coupling reaction could also be exchanged by reaction of a compound of formula 5 to the carboxylic acids of formula 1 which are subsequently converted to the final compounds of formula I.

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the preparations and examples herein below. However, other equivalent separation or isolation procedures could, of course, also be used. Racemic mixtures of chiral compounds of formula I can be separated using chiral HPLC.

Salts of Compounds of Formula I

The compounds of formula I are basic and may be converted to a corresponding acid addition salt. The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or may be brought out of solution with a less polar solvent.

The acid addition salts of the basic compounds of formula I may be converted to the corresponding free bases by treatment with at least a stoichiometric equivalent of a suitable base such as sodium or potassium hydroxide, potassium carbonate, sodium bicarbonate, ammonia, and the like.

The compounds of formula I and their pharmaceutically usable addition salts possess valuable pharmacological properties. Specifically, it has been found that the compounds of the present invention have an activity as neurogenic agents.

The compounds were investigated in accordance with the test given hereinafter.

Neurogenesis Assay

Neural Stem Cell Proliferation Assay

Neurogenic properties of small molecules are determined based on the proliferation of human embryonic stem cell derived neural stem cells (NSCs) which were derived via a dual smad inhibition as previously described (Chambers, S. M., et al., *Highly efficient neural conversion of human ES and iPS cells by dual inhibition of SMAD signaling*, Nature biotechnology, 2009. 27(3): p. 275-80.)

Compounds respond is measured by the increase in cells based on ATP levels (Promega:CellTiterGlo®) after an incubation period of 4 days.

NSCs are thawed and expanded over 3 passages. On the $14^{th}$ day, NSCs are seeded in Polyornithin/Laminin coated 384 well plates at a cell density of 21,000 cells/$cm^2$ in a media volume of 38 µl.

4 hours after cell seeding, compound solutions are added at a volume of 2 µl. Stock solutions of the compounds (water, 5% DMSO) are diluted to obtain a dose response (11 points, dilution factor is 2), ranging from 8 µM to 8 nM. Controls are run to consistently determine the neurogenic properties of the cells:

Negative (neutral) control is cell culture Media (final DMSO concentration: 0.25%).

Positive controls are:
1. cell culture Media+100 ng/ml FGF2 (final DMSO concentration: 0.1%)
2. cell culture Media+20 ng/ml EGF (final DMSO concentration: 0.1%)
3. cell culture Media+100 ng/ml Wnt3a (final DMSO concentration: 0.1%)

After 4 days incubation at 37° C., 5% $CO_2$, the amount of ATP per well is quantified. The ATP concentration is proportional to the cell number. ATP is quantified by using the Promega CellTiterGlo® kit. The CellTiterGlo® reagents contain a cell lysis buffer, a thermo stable luciferase (Ultra-Glo™ recombinant luciferase), magnesium and luciferin. Luciferin reacts with ATP producing oxyluciferin, AMP and light. The luminescence signal is proportional to the ATP content.

The value of negative (neutral) control is determined for each assay plate by taking the average of 16 negative control wells. The neurogenic compound response is calculated for each compound as (compound/Negative Control)*100.

The values of $EC_{150}$ from the dose response curve are determined for each test compound. The $EC_{150}$ is the compound concentration at which 150% activity of control (100%) is reached. The preferred compounds show a $EC_{150}$ (μM) in the range of <2.5 μM as shown in Table 1 below.

TABLE 1

List of examples and $EC_{150}$ data of novel compounds

| Example | Structure | Name | $EC_{150}$ (μM) |
|---|---|---|---|
| 1 | 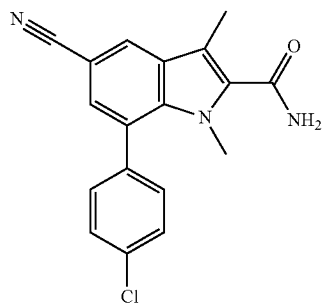 [SMILES: Cc1c(C(N)=O)n(C)c2c(-c3ccc(Cl)cc3)cc(C#N)cc12] | 7-(4-Chlorophenyl)-5-cyano-1,3-dimethylindole-2-carboxamide | 0.14 |
| 2 | 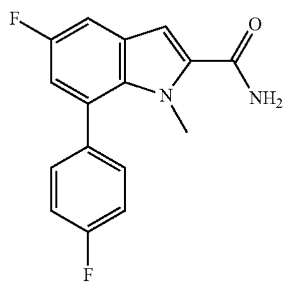 [SMILES: Cn1c(C(N)=O)cc2cc(F)cc(-c3ccc(F)cc3)c21] | 5-Fluoro-7-(4-fluorophenyl-1-methylindole-2-carboxamide | 1.4 |
| 3 | 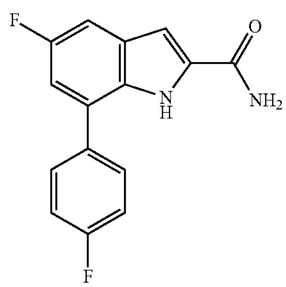 [SMILES: NC(=O)c1cc2cc(F)cc(-c3ccc(F)cc3)c2[nH]1] | 5-Fluoro-7-(4-fluorophenyl)-1H-indole-2-carboxamide | 0.18 |
| 4 | 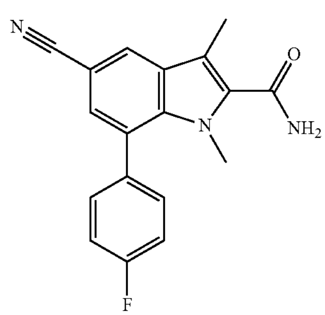 [SMILES: Cc1c(C(N)=O)n(C)c2c(-c3ccc(F)cc3)cc(C#N)cc12] | 5-Cyano-7-(4-fluorophenyl)-1,3-dimethylindole-2-carboxamide | 0.21 |

TABLE 1-continued

List of examples and EC$_{150}$ data of novel compounds

| Example | Structure | Name | EC$_{150}$ (μM) |
|---|---|---|---|
| 5 | 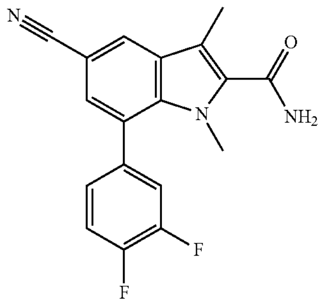 [SMILES: Cc1c(C(N)=O)n(C)c2c(-c3ccc(F)c(F)c3)cc(C#N)cc12] | 5-Cyano-7-(3,4-difluorophenyl)-1,3-dimethylindole-2-carboxamide | 0.35 |
| 6 | 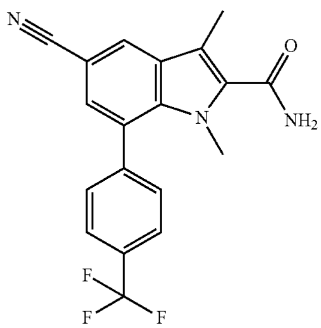 [SMILES: Cc1c(C(N)=O)n(C)c2c(-c3ccc(C(F)(F)F)cc3)cc(C#N)cc12] | 5-Cyano-1,3-dimethyl-7-[4-(trifluoromethyl)-phenyl]-indole-2-carboxamide | 2.7 |
| 7 | 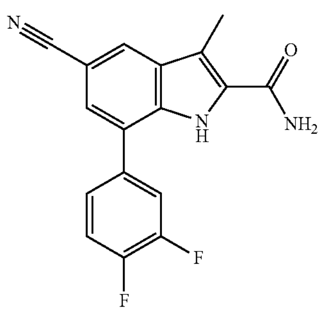 [SMILES: Cc1c(C(N)=O)[nH]c2c(-c3ccc(F)c(F)c3)cc(C#N)cc12] | 5-Cyano-7-(3,4-difluorophenyl)-3-methyl-1H-indole-2-carboxamide | 0.3 |
| 8 | 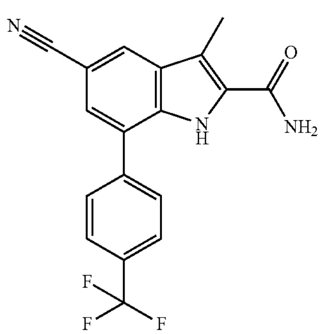 [SMILES: Cc1c(C(N)=O)[nH]c2c(-c3ccc(C(F)(F)F)cc3)cc(C#N)cc12] | 5-Cyano-3-methyl-7-[4-(trifluoromethyl)phenyl]-1H-indole-2-carboxamide | 0.4 |

TABLE 1-continued

List of examples and EC$_{150}$ data of novel compounds

| Example | Structure | Name | EC$_{150}$ (μM) |
|---|---|---|---|
| 9 | 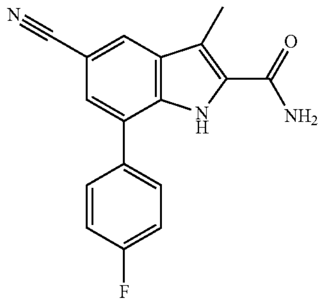 [SMILES: Cc1c(C(N)=O)[nH]c2c(-c3ccc(F)cc3)cc(C#N)cc12] | 5-Cyano-7-(4-fluorophenyl)-3-methyl-1H-indole-2-carboxamide | 0.22 |
| 10 | 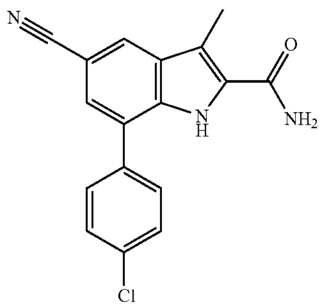 [SMILES: Cc1c(C(N)=O)[nH]c2c(-c3ccc(Cl)cc3)cc(C#N)cc12] | 7-(4-Chlorophenyl)-5-cyano-3-methyl-1H-indole-2-carboxamide | 0.21 |
| 11 | 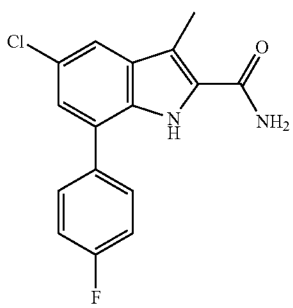 [SMILES: Cc1c(C(N)=O)[nH]c2c(-c3ccc(F)cc3)cc(Cl)cc12] | 5-Chloro-7-(4-fluorophenyl)-3-methyl-1H-indole-2-carboxamide | 0.22 |
| 12 | 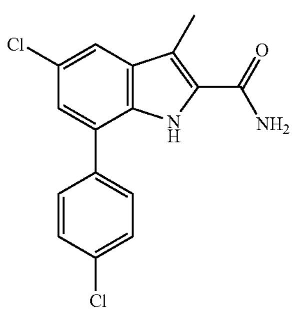 [SMILES: Cc1c(C(N)=O)[nH]c2c(-c3ccc(Cl)cc3)cc(Cl)cc12] | 5-Chloro-7-(4-chlorophenyl)-3-methyl-1H-indole-2-carboxamide | 0.31 |
| 13 | 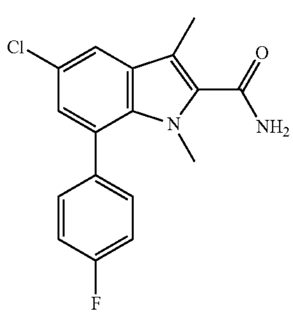 [SMILES: Cc1c(C(N)=O)n(C)c2c(-c3ccc(F)cc3)cc(Cl)cc12] | 5-Chloro-7-(4-fluorophenyl)-1,3-dimethylindole-2-carboxamide | 1.64 |

TABLE 1-continued

List of examples and EC$_{150}$ data of novel compounds

| Example | Structure | Name | EC$_{150}$ (μM) |
|---|---|---|---|
| 14 | 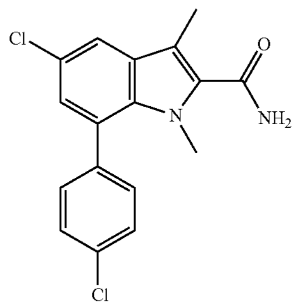 [SMILES: Cc1c(C(N)=O)n(C)c2c(-c3ccc(Cl)cc3)cc(Cl)cc12] | 5-Chloro-7-(4-chlorophenyl)-1,3-dimethylindole-2-carboxamide | 0.84 |
| 15 | 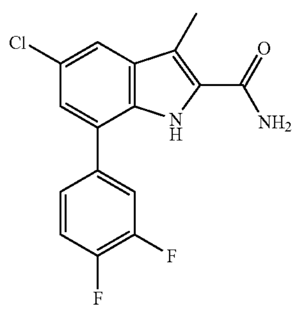 [SMILES: Cc1c(C(N)=O)[nH]c2c(-c3ccc(F)c(F)c3)cc(Cl)cc12] | 5-Chloro-7-(3,4-difluorophenyl)-3-methyl-1H-indole-2-carboxamide | 0.64 |
| 16 | 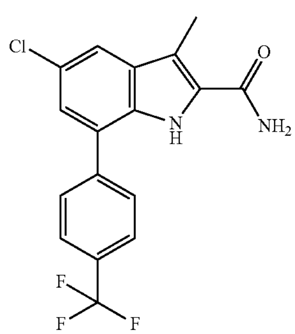 [SMILES: Cc1c(C(N)=O)[nH]c2c(-c3ccc(C(F)(F)F)cc3)cc(Cl)cc12] | 5-Chloro-3-methyl-7-[4-(trifluoromethyl)phenyl]-1H-indole-2-carboxamide | 0.75 |
| 17 | 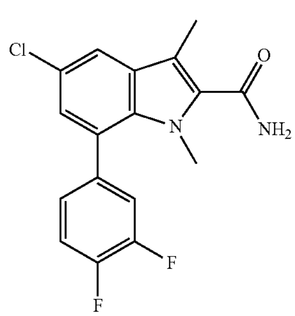 | 5-Chloro-7-(3,4-difluorophenyl)-1,3-dimethylindole-2-carboxamide | 3.3 |

TABLE 1-continued

List of examples and EC$_{150}$ data of novel compounds

| Example | Structure | Name | EC$_{150}$ (µM) |
|---|---|---|---|
| 18 | 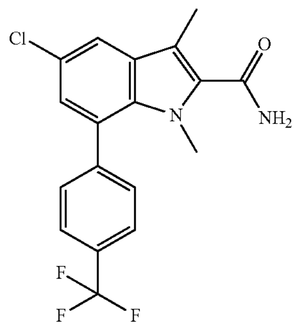 [SMILES: Cc1c(C(N)=O)n(C)c2c(-c3ccc(C(F)(F)F)cc3)cc(Cl)cc12] | 5-Chloro-1,3-dimethyl-7-[4-(trifluoromethyl)phenyl]indole-2-carboxamide | 2.8 |
| 19 | 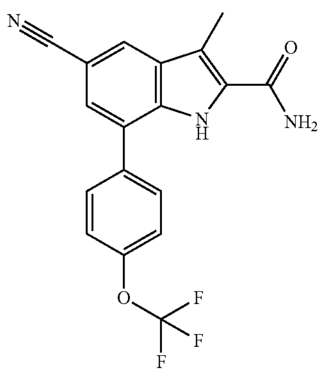 [SMILES: Cc1c(C(N)=O)[nH]c2c(-c3ccc(OC(F)(F)F)cc3)cc(C#N)cc12] | 5-Cyano-3-methyl-7-[4-(trifluoromethoxy)-phenyl]-1H-indole-2-carboxamide | 1.13 |
| 20 | 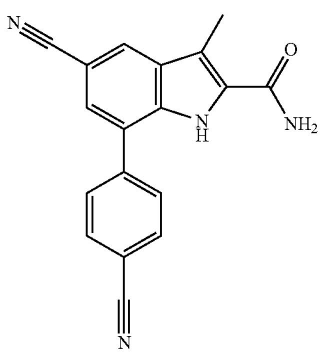 [SMILES: Cc1c(C(N)=O)[nH]c2c(-c3ccc(C#N)cc3)cc(C#N)cc12] | 5-Cyano-7-(4-cyanophenyl)-3-methyl-1H-indole-2-carboxamide | 0.24 |
| 21 | 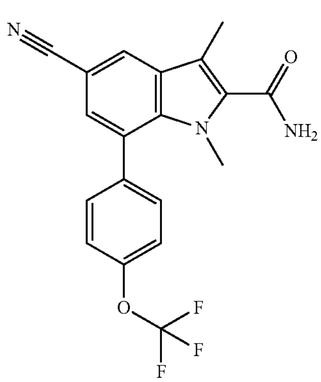 [SMILES: Cc1c(C(N)=O)n(C)c2c(-c3ccc(OC(F)(F)F)cc3)cc(C#N)cc12] | 5-Cyano-1,3-dimethyl-7-[4-(trifluoromethoxy)phenyl]indole-2-carboxamide | 0.43 |

TABLE 1-continued

List of examples and EC$_{150}$ data of novel compounds

| Example | Name | EC$_{150}$ (μM) |
|---|---|---|
| 22 | 5-Cyano-7-(4-cyanophenyl)-1,3-dimethylindole-2-carboxamide | 0.6 |
| 23 | 5-Chloro-7-(4-cyanophenyl)-3-methyl-1H-indole-2-carboxamide | 0.28 |
| 24 | 5-Chloro-3-methyl-7-[4-(trifluoromethoxy)phenyl]-1H-indole-2-carboxamide | 1.32 |
| 25 | 5-Chloro-7-(2,4-difluorophenyl)-3-methyl-1H-indole-2-carboxamide | 0.21 |

TABLE 1-continued

List of examples and EC$_{150}$ data of novel compounds

| Example | Structure | Name | EC$_{150}$ (µM) |
|---|---|---|---|
| 26 | 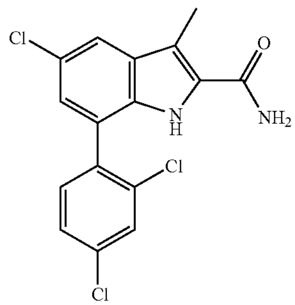 [SMILES: Cc1c(C(N)=O)[nH]c2c(-c3ccc(Cl)cc3Cl)cc(Cl)cc12] | 5-Chloro-7-(2,4-dichlorophenyl)-3-methyl-1H-indole-2-carboxamide | 0.33 |
| 27 | 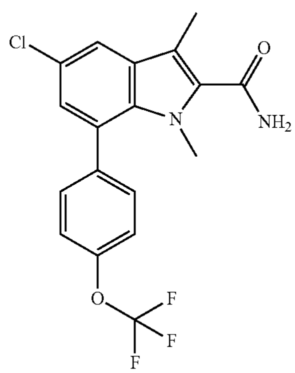 [SMILES: Cc1c(C(N)=O)n(C)c2c(-c3ccc(OC(F)(F)F)cc3)cc(Cl)cc12] | 5-Chloro-1,3-dimethyl-7-[4-(trifluoromethoxy)-phenyl]indole-2-carboxamide | 3.67 |
| 28 | 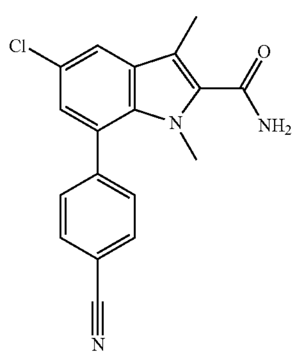 [SMILES: Cc1c(C(N)=O)n(C)c2c(-c3ccc(C#N)cc3)cc(Cl)cc12] | 5-Chloro-7-(4-cyanophenyl)-1,3-dimethylindole-2-carboxamide | 1.06 |
| 29 | 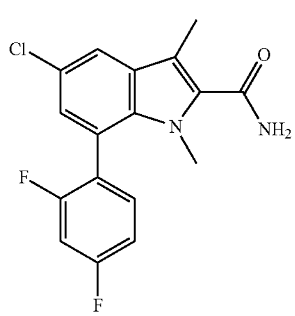 [SMILES: Cc1c(C(N)=O)n(C)c2c(-c3ccc(F)cc3F)cc(Cl)cc12] | 5-Chloro-7-(2,4-difluorophenyl)-1,3-dimethylindole-2-carboxamide | 0.23 |

TABLE 1-continued

List of examples and EC$_{150}$ data of novel compounds

| Example | Structure | Name | EC$_{150}$ (μM) |
|---|---|---|---|
| 30 | 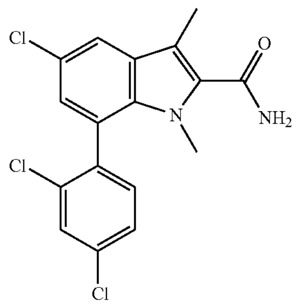 [SMILES: Cc1c(C(N)=O)n(C)c2c(-c3ccc(Cl)cc3Cl)cc(Cl)cc12] | 5-Chloro-7-(2,4-dichlorophenyl)-1,3-dimethylindole-2-carboxamide | 0.93 |
| 31 | 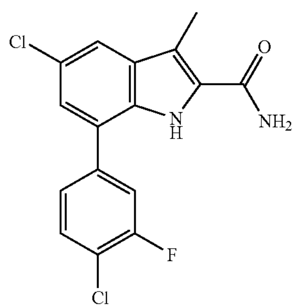 [SMILES: Cc1c(C(N)=O)[nH]c2c(-c3ccc(Cl)c(F)c3)cc(Cl)cc12] | 5-Chloro-7-(4-chloro-3-fluorophenyl)-3-methyl-1H-indole-2-carboxamide | 0.43 |
| 32 | 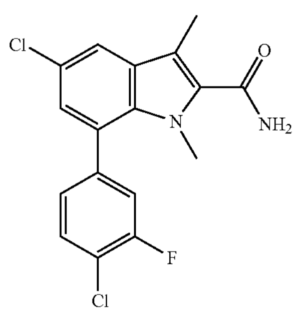 [SMILES: Cc1c(C(N)=O)n(C)c2c(-c3ccc(Cl)c(F)c3)cc(Cl)cc12] | 5-Chloro-7-(4-chloro-3-fluorophenyl)-1,3-dimethylindole-2-carboxamide | 1.02 |
| 33 | 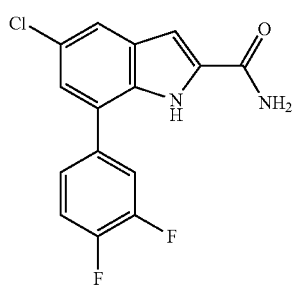 [SMILES: NC(=O)c1cc2cc(Cl)cc(-c3ccc(F)c(F)c3)c2[nH]1] | 5-Cyano-7-(3,4-difluorophenyl)-1H-indole-2-carboxamide | 0.056 |
| 34 | 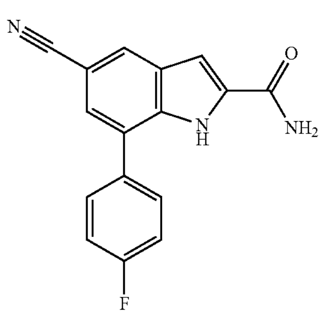 [SMILES: N#Cc1cc(-c2ccc(F)cc2)c2[nH]c(C(N)=O)cc2c1] | 5-Cyano-7-(4-fluorophenyl)-1H-indole-2-carboxamide | 0.057 |

TABLE 1-continued

List of examples and EC$_{150}$ data of novel compounds

| Example | Structure | Name | EC$_{150}$ (μM) |
|---|---|---|---|
| 35 | 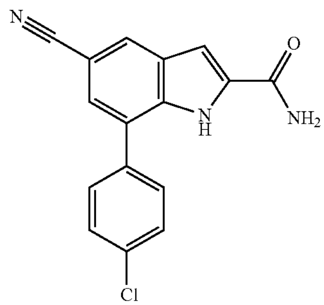 [SMILES: N#Cc1cc(-c2ccc(Cl)cc2)c2[nH]c(C(N)=O)cc2c1] | 7-(4-Chlorophenyl)-5-cyano-1H-indole-2-carboxamide | 0.021 |
| 36 | 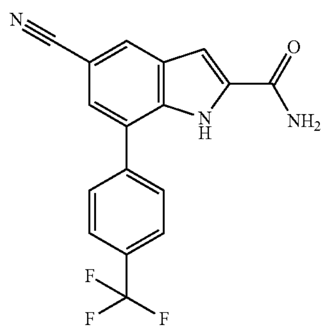 [SMILES: N#Cc1cc(-c2ccc(C(F)(F)F)cc2)c2[nH]c(C(N)=O)cc2c1] | 5-Cyano-7-[4-(trifluoromethyl)phenyl]-1H-indole-2-carboxamide | 0.1 |
| 37 | 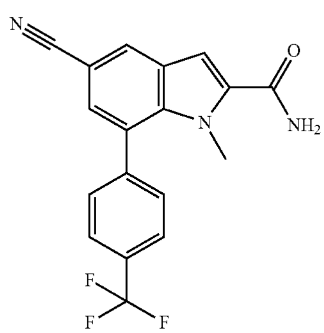 [SMILES: Cn1c(C(N)=O)cc2cc(C#N)cc(-c3ccc(C(F)(F)F)cc3)c21] | 5-Cyano-1-methyl-7-[4-(trifluoromethyl)phenyl]-indole-2-carboxamide | 2.62 |
| 38 | 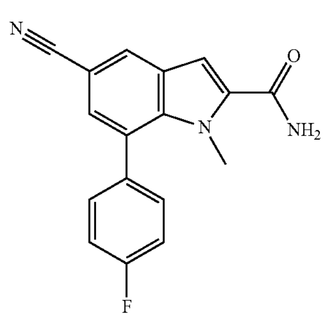 [SMILES: Cn1c(C(N)=O)cc2cc(C#N)cc(-c3ccc(F)cc3)c21] | 5-Cyano-7-(4-fluorophenyl)-1-methylindole-2-carboxamide | 0.19 |

TABLE 1-continued

List of examples and EC$_{150}$ data of novel compounds

| Example | Structure | Name | EC$_{150}$ (μM) |
|---|---|---|---|
| 39 | 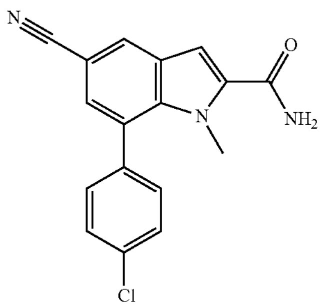 [SMILES: Cn1c(C(N)=O)cc2cc(C#N)cc(-c3ccc(Cl)cc3)c21] | 7-(4-Chlorophenyl)-5-cyano-1-methylindole-2-carboxamide | 0.18 |
| 40 | 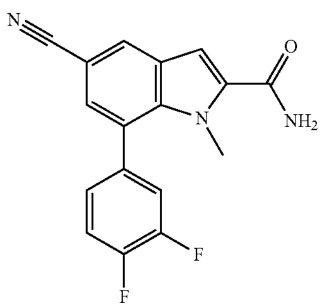 [SMILES: Cn1c(C(N)=O)cc2cc(C#N)cc(-c3ccc(F)c(F)c3)c21] | 5-Cyano-7-(3,4-difluorophenyl)-1-methylindole-2-carboxamide | 0.2 |
| 41 | 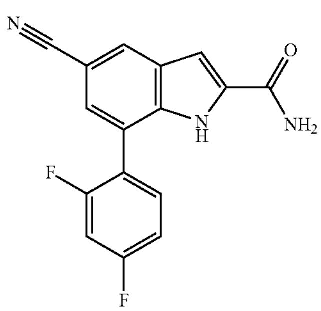 [SMILES: N#Cc1cc(-c2ccc(F)cc2F)c2[nH]c(C(N)=O)cc2c1] | 5-Cyano-7-(2,4-difluorophenyl)-1H-indole-2-carboxamide | 0.025 |
| 42 | 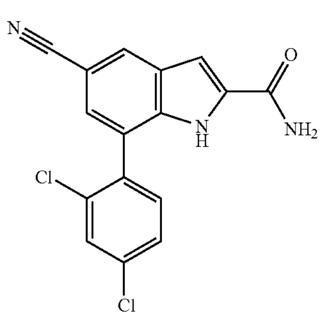 [SMILES: N#Cc1cc(-c2ccc(Cl)cc2Cl)c2[nH]c(C(N)=O)cc2c1] | 5-Cyano-7-(2,4-dichlorophenyl)-1H-indole-2-carboxamide | 0.047 |

TABLE 1-continued

List of examples and EC$_{150}$ data of novel compounds

| Example | Structure | Name | EC$_{150}$ (µM) |
|---|---|---|---|
| 43 | 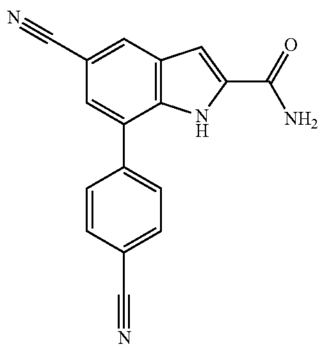 [SMILES: N#Cc1ccc(-c2cc(C#N)cc3cc(C(N)=O)[nH]c23)cc1] | 5-Cyano-7-(4-cyanophenyl)-1H-indole-2-carboxamide | 0.2 |
| 44 | 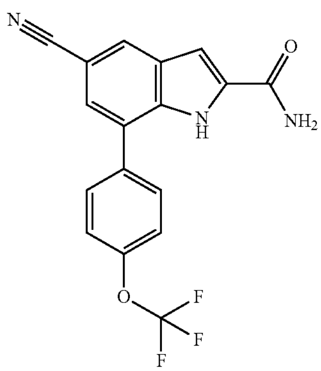 [SMILES: N#Cc1cc(-c2ccc(OC(F)(F)F)cc2)c2[nH]c(C(N)=O)cc2c1] | 5-Cyano-7-[4-(trifluoromethoxy)-phenyl]-1H-indole-2-carboxamide | 0.17 |
| 45 | 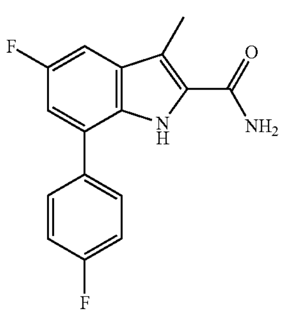 [SMILES: Cc1c(C(N)=O)[nH]c2c(-c3ccc(F)cc3)cc(F)cc12] | 5-Fluoro-7-(4-fluorophenyl)-3-methyl-1H-indole-2-carboxamide | 0.068 |
| 46 | 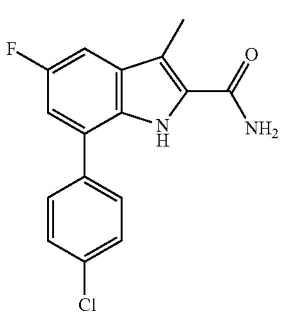 [SMILES: Cc1c(C(N)=O)[nH]c2c(-c3ccc(Cl)cc3)cc(F)cc12] | 7-(4-Chlorophenyl)-5-fluoro-3-methyl-1H-indole-2-carboxamide | 0.066 |

TABLE 1-continued

List of examples and EC$_{150}$ data of novel compounds

| Example | Structure | Name | EC$_{150}$ (μM) |
|---|---|---|---|
| 47 | 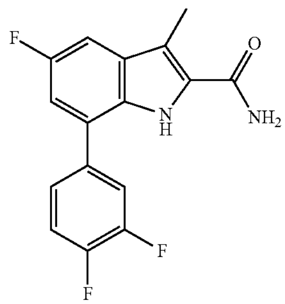 [SMILES: Cc1c(C(N)=O)[nH]c2c(-c3ccc(F)c(F)c3)cc(F)cc12] | 7-(3,4-Difluorophenyl)-5-fluoro-3-methyl-1H-indole-2-carboxamide | 0.052 |
| 48 | 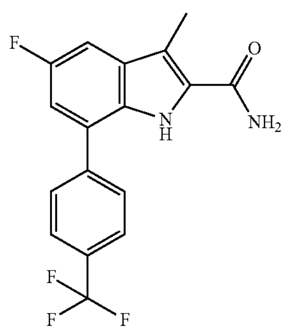 [SMILES: Cc1c(C(N)=O)[nH]c2c(-c3ccc(C(F)(F)F)cc3)cc(F)cc12] | 5-Fluoro-3-methyl-7-[4-(trifluoromethyl)-phenyl]-1H-indole-2-carboxamide | 0.11 |
| 49 | 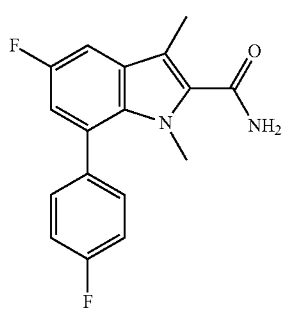 [SMILES: Cc1c(C(N)=O)n(C)c2c(-c3ccc(F)cc3)cc(F)cc12] | 5-Fluoro-7-(4-fluorophenyl)-1,3-dimethylindole-2-carboxamide | 0.17 |
| 50 | 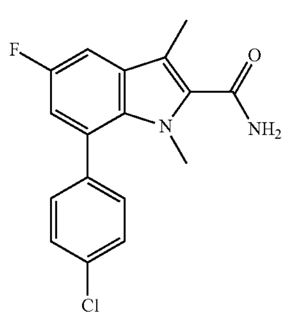 [SMILES: Cc1c(C(N)=O)n(C)c2c(-c3ccc(Cl)cc3)cc(F)cc12] | 7-(4-Chlorophenyl)-5-fluoro-1,3-dimethylindole-2-carboxamide | 0.12 |

TABLE 1-continued

List of examples and EC$_{150}$ data of novel compounds

| Example | Structure | Name | EC$_{150}$ (μM) |
|---|---|---|---|
| 51 | 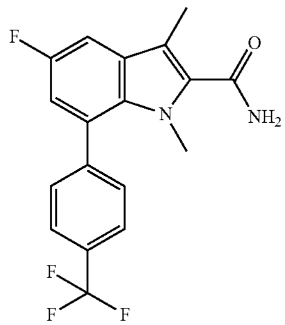 [SMILES: Cc1c(C(N)=O)n(C)c2c(-c3ccc(C(F)(F)F)cc3)cc(F)cc12] | 5-Fluoro-1,3-dimethyl-7-[4-(trifluoromethyl)-phenyl]-indole-2-carboxamide | 0.13 |
| 52 | 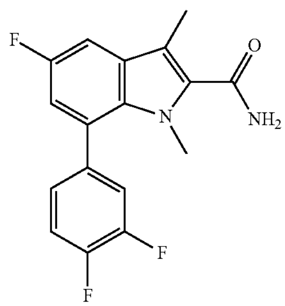 [SMILES: Cc1c(C(N)=O)n(C)c2c(-c3ccc(F)c(F)c3)cc(F)cc12] | 7-(3,4-Difluorophenyl)-5-fluoro-1,3-dimethylindole-2-carboxamide | 0.7 |
| 53 | 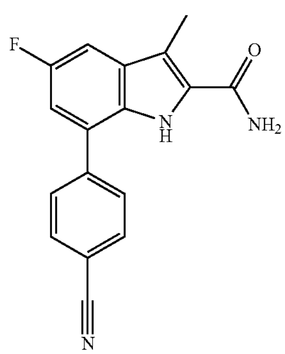 [SMILES: Cc1c(C(N)=O)[nH]c2c(-c3ccc(C#N)cc3)cc(F)cc12] | 7-(4-Cyanophenyl)-5-fluoro-3-methyl-1H-indole-2-carboxamide | 0.04 |
| 54 | 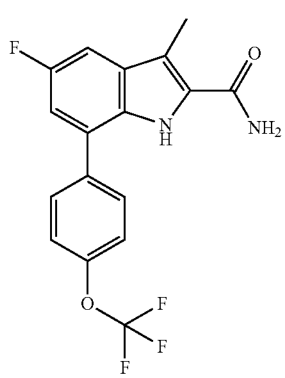 [SMILES: Cc1c(C(N)=O)[nH]c2c(-c3ccc(OC(F)(F)F)cc3)cc(F)cc12] | 5-Fluoro-3-methyl-7-[4-(trifluoromethoxy)phenyl]-1H-indole-2-carboxamide | 0.2 |

TABLE 1-continued

List of examples and EC$_{150}$ data of novel compounds

| Example | Structure | Name | EC$_{150}$ (µM) |
|---|---|---|---|
| 55 | 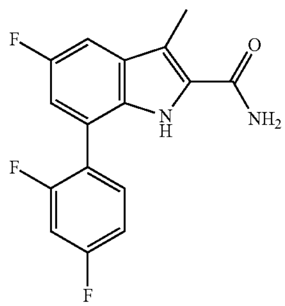 [SMILES: Cc1c(C(N)=O)[nH]c2c(-c3ccc(F)cc3F)cc(F)cc12] | 7-(2,4-Difluorophenyl)-5-fluoro-3-methyl-1H-indole-2-carboxamide | 0.026 |
| 56 | 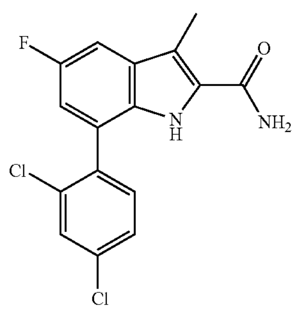 [SMILES: Cc1c(C(N)=O)[nH]c2c(-c3ccc(Cl)cc3Cl)cc(F)cc12] | 7-(2,4-Dichlorophenyl)-5-fluoro-3-methyl-1H-indole-2-carboxamide | 0.027 |
| 57 | 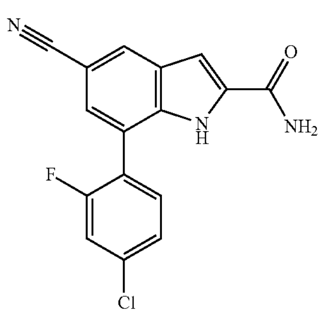 [SMILES: N#Cc1cc(-c2ccc(Cl)cc2F)c2[nH]c(C(N)=O)cc2c1] | 7-(4-Chloro-2-fluorophenyl)-5-cyano-1H-indole-2-carboxamide | 0.066 |
| 58 | 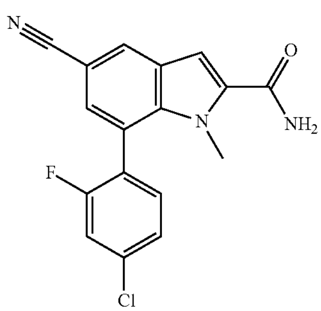 [SMILES: Cn1c(C(N)=O)cc2cc(C#N)cc(-c3ccc(Cl)cc3F)c21] | 7-(4-Chloro-2-fluorophenyl)-5-cyano-1-methylindole-2-carboxamide | 1.67 |

TABLE 1-continued
List of examples and EC$_{150}$ data of novel compounds
| Example | Structure | Name | EC$_{150}$ (μM) |
|---|---|---|---|
| 59 | 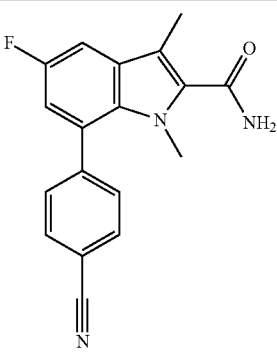 [SMILES: Cc1c(C(N)=O)n(C)c2c(-c3ccc(C#N)cc3)cc(F)cc12] | 7-(4-Cyanophenyl)-5-fluoro-1,3-dimethylindole-2-carboxamide | 0.083 |
| 60 | 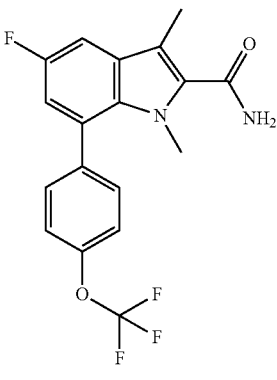 [SMILES: Cc1c(C(N)=O)n(C)c2c(-c3ccc(OC(F)(F)F)cc3)cc(F)cc12] | 5-Fluoro-1,3-dimethyl-7-[4-(trifluoromethoxy)phenyl]indole-2-carboxamide | 0.22 |
| 61 | 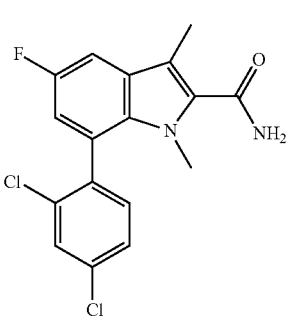 [SMILES: Cc1c(C(N)=O)n(C)c2c(-c3ccc(Cl)cc3Cl)cc(F)cc12] | 7-(2,4-Dichlorophenyl)-5-fluoro-1,3-dimethylindole-2-carboxamide | 0.21 |
| 62 | 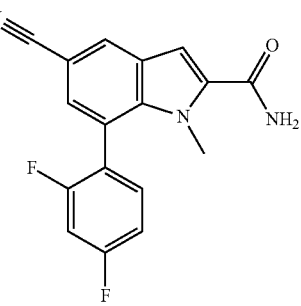 | 5-Cyano-7-(2,4-difluorophenyl)-1-methylindole-2-carboxamide | 0.12 |

TABLE 1-continued

List of examples and EC$_{150}$ data of novel compounds

| Example | Name | EC$_{150}$ (μM) |
|---|---|---|
| 63 | 5-Cyano-7-(2,4-dichlorophenyl)-1-methylindole-2-carboxamide | 0.21 |
| 64 | 7-(2,4-Difluorophenyl)-5-fluoro-1,3-dimethylindole-2-carboxamide | 0.091 |
| 65 | 5-Cyano-7-(4-fluoro-3-methylphenyl)-1-methylindole-2-carboxamide | 0.18 |
| 66 | 5-Cyano-7-(4-fluoro-3-methylphenyl)-1H-indole-2-carboxamide | 0.62 |
| 67 | 5-Cyano-1-methyl-7-(4-nitrophenyl)-indole-2-carboxamide | 2.05 |

TABLE 1-continued

List of examples and EC$_{150}$ data of novel compounds

| Example | Structure | Name | EC$_{150}$ (μM) |
|---|---|---|---|
| 68 | 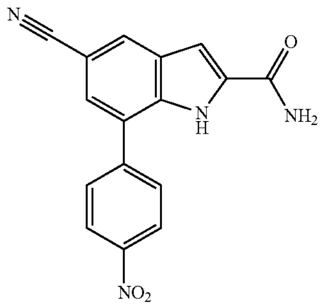 [SMILES: N#Cc1cc(-c2ccc([N+](=O)[O-])cc2)c2[nH]c(C(N)=O)cc2c1] | 5-Cyano-7-(4-nitrophenyl)-1H-indole-2-carboxamide | 0.071 |
| 69 | 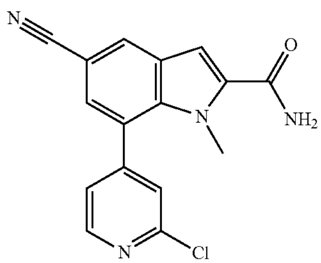 [SMILES: Cn1c(C(N)=O)cc2cc(C#N)cc(-c3ccnc(Cl)c3)c21] | 7-(2-Chloropyridin-4-yl)-5-cyano-1-methylindole-2-carboxamide | 0.13 |
| 70 | 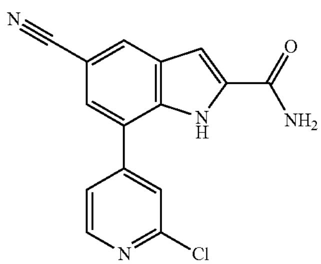 [SMILES: N#Cc1cc(-c2ccnc(Cl)c2)c2[nH]c(C(N)=O)cc2c1] | 7-(2-Chloropyridin-4-yl)-5-cyano-1H-indole-2-carboxamide | 0.14 |
| 71 | 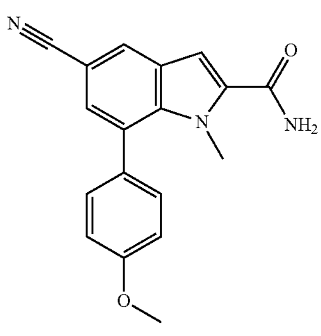 [SMILES: COc1ccc(-c2cc(C#N)cc3cc(C(N)=O)n(C)c23)cc1] | 5-Cyano-7-(4-methoxyphenyl)-1-methylindole-2-carboxamide | 0.21 |
| 72 | 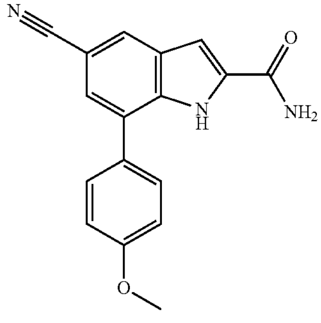 [SMILES: COc1ccc(-c2cc(C#N)cc3cc(C(N)=O)[nH]c23)cc1] | 5-Cyano-7-(4-methoxyphenyl)-1H-indole-2-carboxamide | 0.19 |

TABLE 1-continued
List of examples and EC$_{150}$ data of novel compounds
| Example | Structure | Name | EC$_{150}$ (µM) |
|---|---|---|---|
| 73 | 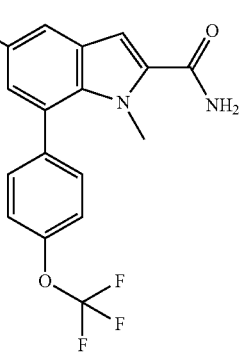 | 5-Cyano-1-methyl-7-[4-(trifluoromethoxy)phenyl]indole-2-carboxamide | 7.5 |
| 74 | 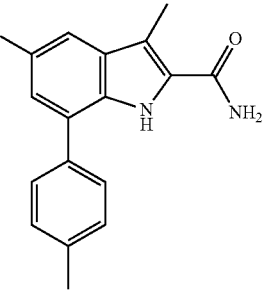 | 5-Fluoro-3-methyl-7-(4-methylphenyl)-1H-indole-2-carboxamide | 0.17 |
| 75 | 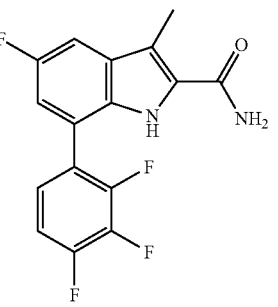 | 5-Fluoro-3-methyl-7-(2,3,4-trifluorophenyl)-1H-indole-2-carboxamide | 0.082 |
| 76 | 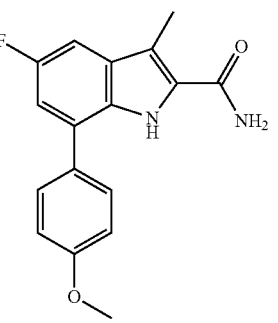 | 5-Fluoro-7-(4-methoxyphenyl)-3-methyl-1H-indole-2-carboxamide | 0.009 |

TABLE 1-continued

List of examples and EC$_{150}$ data of novel compounds

| Example | Structure | Name | EC$_{150}$ (μM) |
|---|---|---|---|
| 77 | 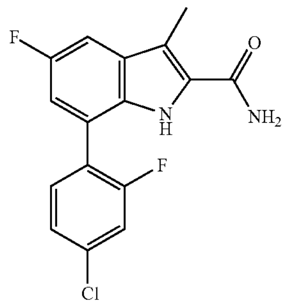 [SMILES: Cc1c(C(N)=O)[nH]c2c(-c3ccc(Cl)cc3F)cc(F)cc12] | 7-(4-Chloro-2-fluorophenyl)-5-fluoro-3-methyl-1H-indole-2-carboxamide | 0.022 |
| 78 | 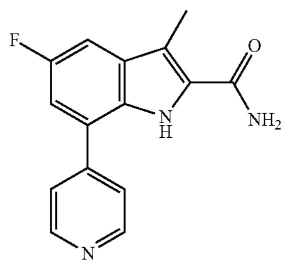 [SMILES: Cc1c(C(N)=O)[nH]c2c(-c3ccncc3)cc(F)cc12] | 5-Fluoro-3-methyl-7-pyridin-4-yl-1H-indole-2-carboxamide | 0.053 |

The compounds of formula I and the pharmaceutically acceptable salts of the compounds of formula I can be used as medicaments, e.g. in the form of pharmaceutical preparations. The pharmaceutical preparations can be administered orally, e.g. in the form of tablets, coated tablets, dragees, hard and soft gelatine capsules, solutions, emulsions or suspensions. The administration can, however, also be effected rectally, e.g. in the form of suppositories, or parenterally, e.g. in the form of injection solutions.

The compounds of formula I can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragees and hard gelatine capsules. Suitable carriers for soft gelatine capsules are, for example, vegetable oils, waxes, fats, semi-solid and liquid polyols and the like. Depending on the nature of the active substance no carriers are however usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula I or a pharmaceutically acceptable salt thereof and a therapeutically inert carrier are also an object of the present invention, as is a process for their production, which comprises bringing one or more compounds of formula I and/or pharmaceutically acceptable acid addition salts and, if desired, one or more other therapeutically valuable substances into a galenical administration form together with one or more therapeutically inert carriers.

The most preferred indications in accordance with the present invention are those which include disorders of the central nervous system, for example the treatment or prevention of depression, psychosis, Parkinson's disease, anxiety, attention deficit hyperactivity disorder (ADHD) and diabetes.

The dosage can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

Tablet Formulation (Wet Granulation)

| | | mg/tablet | | | |
|---|---|---|---|---|---|
| Item mg | Ingredients | 5 mg | 25 mg | 100 mg | 500 |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure
1. Mix items 1, 2, 3 and 4 and granulate with purified water.
2. Dry the granules at 50° C.
3. Pass the granules through suitable milling equipment.

4. Add item 5 and mix for three minutes; compress on a suitable press.

Capsule Formulation

| Item mg | Ingredients | 5 mg | 25 mg | 100 mg | 500 |
|---|---|---|---|---|---|
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

Intermediate 1

7-Bromo-5-fluoro-1-methylindole-2-carboxamide

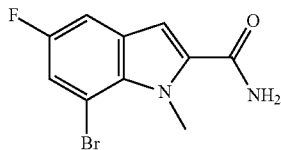

Step A
To a stirred solution of commercially available ethyl 7-bromo-5-fluoro-1H-indole-2-carboxylate [CAS No. 396076-60-1](150 mg, 524 μmol) and cesium carbonate (530 mg, 1.63 mmol) in DMF (2.5 ml) was added at room temperature iodomethane (930 mg, 410 μl, 6.55 mmol) was added and the reaction mixture was allowed to stir at room temperature for 16 h. The reaction mixture was poured into water (30 ml) and extracted with ethyl acetate (2×40 ml). The combined organic layers was washed with brine (1×30 ml), dried (MgSO$_4$) and evaporated to yield ethyl 7-bromo-5-fluoro-1-methylindole-2-carboxylate as a light brown solid (157 mg, 99%), MS (ISP) m/z=300.4 [(M+H)$^+$], mp 58° C.

Step B
A solution of ethyl 7-bromo-5-fluoro-1-methylindole-2-carboxylate (step A) (150 mg, 500 μmol) in 1 M potassium hydroxide solution in MeOH (5 ml, 5.0 mmol) and water (2.5 ml) was stirred for 45 min at 60° C. The reaction mixture was cooled to room temperature and acified with 2M hydrochloric acid solution (3 ml), the solid was filtered off, diluted in dichloromethane/MeOH 9:1, the solution was dried (MgSO$_4$) and evaporated to yield 7-bromo-5-fluoro-1-methylindole-2-carboxylic acid as an off-white solid (132 mg, 97%), MS (ISN) m/z=272.4 [(M−H)$^-$], mp 245° C.

Step C
A stirred solution of 7-bromo-5-fluoro-1-methylindole-2-carboxylic acid (step B) (125 mg, 459 μmol) in THF (2 ml) was cooled to 0° C., then DMF (20 μl) and oxalyl chloride (117 mg, 80.4 μl, 919 μmol) were added and the reaction mixture was allowed to stir for 90 min at room temperature. The reaction mixture was evaporated to dryness, the residue was suspended in THF (3 ml) and cooled to 0° C. Afterwards 25% ammonium hydroxide solution (546 mg, 600 μl, 4.01 mmol) was added and the reaction mixture was allowed to stir at 0° C. for 10 min, and subsequently at room temperature for 30 min. Water (3 ml) was added, the mixture was allowed to stir for 30 min at room temperature, the precipitated solid was filtered off, washed with water and dried in vacuo to yield the title compound as an off-white solid (125 mg, 100%), MS (ISN) m/z=271.2 [(M−H)$^-$], mp 232° C.

Intermediate 2

7-Bromo-5-fluoro-1H-indole-2-carboxamide

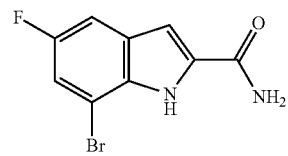

Step A
7-Bromo-5-fluoro-1H-indole-2-carboxylic acid, off-white solid (129 mg, 95%), MS (ISN) m/z=256.4 [(M−H)$^-$], mp 282° C., was prepared in accordance with the general method of intermediate 1, step B, from commercially available ethyl 7-bromo-5-fluoro-1H-indole-2-carboxylate [CAS No. 396076-60-1](0.15 g, 0.52 mmol).

Step B
The title compound, off-white solid (125 mg, 100%), MS (ISN) m/z=257.2 [(M−H)$^-$], mp 188° C., was prepared in accordance with the general method of intermediate 1, step C, from 7-bromo-5-fluoro-1H-indole-2-carboxylic acid (step A) (125 mg, 0.48 mmol).

Intermediate 3

7-Brono-5-cyano-3-methyl-1H-indole-2-carboxamide

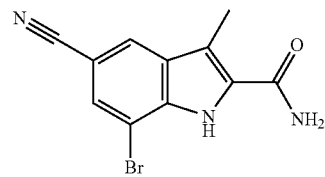

Step A
To a stirred solution of hydrochloric acid (25%, 50 ml) was added commercially available 4-amino-3-bromobenzonitrile (10 g, 50.8 mmol). The reaction mixture was cooled to 0° C. and a solution of sodium nitrite (4.03 g, 58.4 mmol) in water (33 ml) was added drop wise over a period of 20 min while keeping the temperature below 10° C. The reaction mixture was allowed to stir at 0° C. for 1 h, afterwards a solution of tin(II)chloride dihydrate (51.5 g, 228 mmol) in hydrochloric acid (25%, 75.3 ml) was added slowly drop wise at 0° C. while keeping the temperature of the reaction mixture below 10° C. The reaction was allowed to stir for 1 h at 0° C., was basified with sodium hydroxide solution (32%, 220 ml), diluted with water (500 ml) and extracted with dichloromethane (3×500 ml). The combined organic layers were washed with water (2×500 ml), dried (MgSO₄) and evaporated. The crude product (~10 g brown solid) was taken further purified by flash chromatography on silica gel (heptane/ethyl acetate 3:2) and trituration (diethyl ether/heptane to yield (2-bromo-4-cyano-phenyl)-hydrazine as a light brown solid (5.05 g, 47%), MS (ISN) m/z=210.1 [(M−H)⁻], mp 115° C.

Step B (Z)-2-[(2-Bromo-4-cyano-phenyl)-hydrazono]-butyric acid methyl ester (7.33 g, 99%), brown solid, MS (ISN) m/z=310.3 [(M−H)⁻], mp 103° C., was prepared in accordance with the general method of intermediate 5, step B, from (2-bromo-4-cyano-phenyl)-hydrazine (step A) (5.04 g, 23.8 mmol).

Step C

Methyl 7-bromo-5-cyano-3-methyl-1H-indole-2-carboxylate, off-white solid (3.44 g, 50%), MS (ISN) m/z=293.4 [(M−H)⁻], mp 248° C., was prepared in accordance with the general method of intermediate 5, step C, from (Z)-2-[(2-bromo-4-cyano-phenyl)-hydrazono]-butyric acid methyl ester (step B) (7.22 g, 23.3 mmol).

Step D

7-Bromo-5-cyano-3-methyl-1H-indole-2-carboxylic acid, white solid (560 mg, 98%), MS (ISN) m/z=277.2 [(M−H)⁻], mp 288° C., was prepared in accordance with the general method of intermediate 1, step B, from methyl 7-bromo-5-cyano-3-methyl-1H-indole-2-carboxylate (step C) (0.6 g, 2.05 mmol).

Step E

The title compound, off-white solid (457 mg, 82%), MS (ISN) m/z=276.4 [(M−H)⁻], mp 310° C., was prepared in accordance with the general method of intermediate 1, step C, from 7-bromo-5-cyano-3-methyl-1H-indole-2-carboxylic acid (step D) (560 mg, 2.01 mmol).

Intermediate 4

7-Bromo-5-cyano-1,3-dimethylindole-2-carboxamide

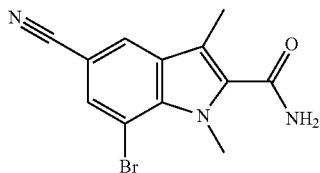 [SMILES: Cc1c(C(N)=O)n(C)c2c(Br)cc(C#N)cc12]

Step A

Methyl 7-bromo-5-cyano-1,3-dimethylindole-2-carboxylate, white solid (0.6 g, 95%), MS (ISP) m/z=309.4 [(M+H)⁺], mp 170° C., was prepared in accordance with the general method of intermediate 1, step A, from methyl 7-bromo-5-cyano-3-methyl-1H-indole-2-carboxylate (intermediate 3, step C) (0.6 g, 2.05 mmol).

Step B

7-Bromo-5-cyano-1,3-dimethylindole-2-carboxylic acid, white solid (0.56 g, 99%), MS (ISN) m/z=293.0 [(M−H)⁻], mp 259° C., was prepared in accordance with the general method of intermediate 1, step B, from methyl 7-bromo-5-cyano-1,3-dimethylindole-2-carboxylate (step A) (595 mg, 1.94 mmol).

Step C

The title compound, off-white solid (482 mg, 86%), MS (ISN) m/z=292.4 [(M−H)⁻], mp 281° C., was prepared in accordance with the general method of intermediate 1, step C, from 7-bromo-5-cyano-1,3-dimethylindole-2-carboxylic acid (step B) (564 mg, 1.92 mmol).

Intermediate 5

7-Bromo-5-chloro-3-methyl-1H-indole-2-carboxamide

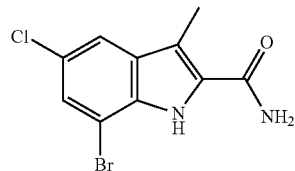

Step A (2-Bromo-4-chloro-phenyl)-hydrazine, off-white solid (1.98 g, 60%), MS (ISP) m/z=223.3 [(M+H)⁺], mp 102° C., was prepared in accordance with the general method of intermediate 3, step A, from commercially available 2-bromo-4-chloro-aniline (3.1 g, 15.0 mmol).

Step B

A stirred solution of (2-bromo-4-chloro-phenyl)-hydrazine (step A) (1.98 g, 8.94 mmol) in ethanol (6.5 ml) was cooled to 0° C. and a solution of commercially available methyl 2-ketobutyrate (1.08 g, 1.04 ml, 9.3 mmol) in ethanol (2 ml) was added drop wise at 0° C. for 15 min. After the mixture was allowed to stir at room temperature for 3 h it was evaporated. The crude material (3.01 g) was purified by flash chromatography on silica gel (heptane/ethyl acetate 0-20%) to yield (Z)-2-[(2-bromo-4-chloro-phenyl)-hydrazono]-butyric acid methyl ester (2.67 g, 94%) as a light yellow solid, MS (ISP) m/z=321.3 [(M+H)⁺], mp 67° C.

Step C

To a stirred solution of (Z)-2-[(2-bromo-4-chloro-phenyl)-hydrazono]-butyric acid methyl ester (step B) (2.67 g, 8.35 mmol) in acetic acid (30 ml) was added at room temperature zinc chloride (6.26 g, 46.0 mmol) and the mixture was allowed to stir for 1 h under reflux conditions. Afterwards the reaction mixture was poured into ice/water (50 ml) and extracted with ethyl acetate (2×50 ml). The combined organic layers were washed with brine (50 ml), dried (MgSO4) and evaporated. The crude product (2.5 g) was further purified by flash chromatography on silica gel (heptane/ethyl acetate 0-20%) and trituration with diethyl ether (5 ml) and heptane (15 ml) to yield methyl 7-bromo-5-chloro-3-methyl-1H-indole-2-carboxylate as an off-white solid (2.02 g, 80%), MS (ISN) m/z=302.3 [(M−H)⁻], mp 163.5° C.

Step D

7-Bromo-5-chloro-3-methyl-1H-indole-2-carboxylic acid, off-white solid (0.75 g, 100%), MS (ISN) m/z=288.4 [(M−H)⁻], mp 277° C., was prepared in accordance with the general method of intermediate 1, step B, from methyl 7-bromo-5-chloro-3-methyl-1H-indole-2-carboxylate (step C) (0.79 g, 2.61 mmol).

Step E

The title compound, white solid (736 mg, 99%), MS (ISN) m/z=287.4 [(M−H)⁻], mp 303° C., was prepared in accordance with the general method of intermediate 1, step C, from 7-bromo-5-chloro-3-methyl-1H-indole-2-carboxylic acid (step D) (745 mg, 2.58 mmol).

Intermediate 6

7-Bromo-5-chloro-1,3-dimethylindole-2-carboxamide

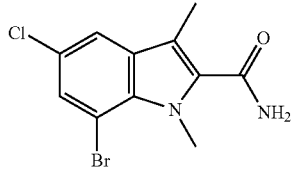 [SMILES: Cc1c(C(N)=O)n(C)c2c(Br)cc(Cl)cc12]

Step A

Methyl 7-bromo-5-chloro-1,3-dimethylindole-2-carboxylate, white solid (0.83 g, 99%), MS (ISP) m/z=318.3 [(M+H)+], mp 113° C., was prepared in accordance with the general method of intermediate 1, step A, from methyl 7-bromo-5-chloro-3-methyl-1H-indole-2-carboxylate (intermediate 5, step C) (0.8 g, 2.64 mmol).

Step B

7-Bromo-5-chloro-1,3-dimethylindole-2-carboxylic acid, off-white solid (0.78 g, 99%), MS (ISN) m/z=302.4 [(M−H)−], mp 251° C., was prepared in accordance with the general method of intermediate 1, step B, from methyl 7-bromo-5-chloro-1,3-dimethylindole-2-carboxylate (step A) (0.82 g, 2.59 mmol).

Step C

The title compound, white solid (766 mg, 99%), MS (ISN) m/z=301.4 [(M−H)−], mp 253° C., was prepared in accordance with the general method of intermediate 1, step C, from 7-bromo-5-chloro-1,3-dimethylindole-2-carboxylic acid (step B) (775 mg, 2.56 mmol).

Intermediate 7

7-Bromo-5-cyano-1H-indole-2-carboxamide

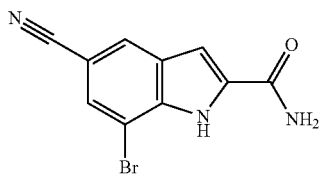 [SMILES: N#Cc1cc(Br)c2[nH]c(C(N)=O)cc2c1]

Step A

To a stirred solution of commercially available 4-amino-3-bromo-5-iodobenzonitrile (0.5 g, 1.55 mmol) in THF (7.7 ml) was added Boc-anhydride (0.71 g, 755 µl, 3.25 mmol) and 4-dimethylaminopyridine (18.9 mg, 155 µmol), and the solution was allowed to stir for 3 h at room temperature. The reaction mixture was evaporated and purified by flash chromatography on silica gel (heptane/ethyl acetate 0-50%) to yield a light yellow solid (0.74 g) which was subsequently solved in dichloromethane (2.2 ml) and cooled to 0° C. Afterwards trifluoroacetic acid (318 mg, 215 µl, 2.79 mmol) was added, and the solution was allowed to stir for 3 h at 0° C. Saturated sodium carbonate solution (5 ml) was added and the mixture was extracted with dichloromethane (2×20 ml). The combined organic layers were washed with brine (30 ml), dried (MgSO4) and evaporated. The crude product (0.69 g) was further purified by flash chromatography on silica gel (heptane/ethyl acetate 0-20%) and crystallization (heptane) to yield (2-bromo-4-cyano-6-iodo-phenyl)-carbamic acid tert-butyl ester (0.42 g, 64%) as an off-white solid, MS (ISN) m/z=421.3 [(M−H)−], mp 117.5° C.

Step B

A mixture of (2-bromo-4-cyano-6-iodo-phenyl)-carbamic acid tert-butyl ester (step A) (413 mg, 0.98 mmol), 3,3-diethoxyprop-1-yne (125 mg, 140 µl, 0.98 mmol), triethylamine (395 mg, 544 µl, 3.9 mmol), copper(I)iodide (5.58 mg, 29.3 µmol) and bis(triphenylphosphine)-palladium(II) chloride (34.3 mg, 48.8 µmol) was allowed to stir for 3 h at room temperature. Afterwards 2,3,4,6,7,8,9,10-octahydro-pyrimido[1,2-a]azepine (297 mg, 292 µl, 1.95 mmol) and DMF (1.58 ml) were added, and the reaction mixture was allowed to stir for 17 h at room temperature, poured into water (10 ml) and extracted with ethyl acetate (2×20 ml). The combined organic layers were washed with brine, dried (MgSO4) and evaporated. The crude product (0.51 g) was further purified by flash chromatography on silica gel (heptane/ethyl acetate 0-20%) to yield 7-bromo-5-cyano-2-diethoxymethyl-indole-1-carboxylic acid tert-butyl ester (0.29 g, 64%) as a light yellow oil, MS (EI) m/z=422 [(M)+].

Step C 7-bromo-5-cyano-2-diethoxymethyl-indole-1-carboxylic acid tert-butyl ester (0.29 g, 685 mol) was solved in THF (2 ml) and cooled to 0° C. Afterwards hydrochloric acid (37%, 1.35 g, 1.14 ml, 13.7 mmol) was added quickly, and the mixture was allowed to stir for 15 min at 0° C. and for 5 h at room temperature. The mixture was cooled (ice bath), saturated sodium carbonate solution (10 ml) was added and the mixture was extracted with ethyl acetate (2×25 ml). The combined organic layers were washed with brine (30 ml), dried (MgSO4) and evaporated. The crude product (0.18 g) was further purified by flash chromatography on silica gel (heptane/ethyl acetate 0-20%) to yield 7-bromo-2-formyl-1H-indole-5-carbonitrile (0.17 g, 100%) as an orange solid, MS (ISN) m/z=247.4 [(M−H)−], mp 117.5° C.

Step D

To a stirred solution of 7-bromo-2-formyl-1H-indole-5-carbonitrile (0.17 g, 683 mol) in MeOH (6.03 ml) was added sodium cyanide (167 mg, 3.41 mmol) and manganese dioxide (297 mg, 3.41 mmol) and the reaction mixture was allowed to stir for 17 h at room temperature. The mixture was evaporated, water (20 ml) was added and the mixture was extracted with ethyl acetate (2×15 ml). The combined organic layers were washed with brine, dried (MgSO4) and evaporated. The crude product (0.11 g) was further purified by flash chromatography on silica gel (heptane/ethyl acetate 0-20%) to yield methyl 7-bromo-5-cyano-1H-indole-2-carboxylate (0.105 g, 55%) as an orange solid, MS (ISN) m/z=279.3 [(M−H)−], mp 248° C.

Step E

7-Bromo-5-cyano-1H-indole-2-carboxylic acid, white solid (0.9 g, 100%), MS (ISN) m/z=265.0 [(M−H)−], mp 310° C., was prepared in accordance with the general method of intermediate 1, step B, from methyl 7-bromo-5-cyano-1H-indole-2-carboxylate (step D) (997 mg, 2.61 mmol).

Step F

The title compound, white solid (880 mg, 99%), MS (ISN) m/z=264.0 [(M−H)−], mp 283.5° C., was prepared in accordance with the general method of intermediate 1, step C, from 7-bromo-5-cyano-1H-indole-2-carboxylic acid (step E) (896 mg, 3.38 mmol).

Intermediate 8

7-Bromo-5-cyano-1-methylindole-2-carboxamide

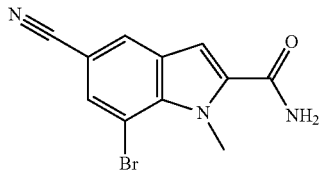 [SMILES: Cn1c(C(N)=O)cc2cc(C#N)cc(Br)c21]

Step A

Ethyl 7-bromo-5-cyano-1-methylindole-2-carboxylate, off-white solid (0.44 g, 96%), MS (ISP) m/z=309.0 [(M+H)$^+$], mp 138° C., was prepared in accordance with the general method of intermediate 1, step A, from ethyl 7-bromo-5-cyano-1H-indole-2-carboxylate (intermediate 7, step D) (0.44 g, 1.5 mmol).

Step B

7-Bromo-5-cyano-1-methylindole-2-carboxylic acid, white solid (0.4 g, 100%), MS (ISN) m/z=277.3 [(M−H)$^-$], mp 287° C., was prepared in accordance with the general method of intermediate 1, step B, from ethyl 7-bromo-5-cyano-1-methylindole-2-carboxylate (step A) (0.44 g, 1.43 mmol).

Step C

The title compound, white solid (370 mg, 93%), MS (ISN) m/z=276.0 [(M−H)$^-$], mp 237.5° C., was prepared in accordance with the general method of intermediate 1, step C, from 7-bromo-5-cyano-1-methylindole-2-carboxylic acid (step B) (0.4 g, 1.43 mmol).

Intermediate 9

7-Bromo-5-fluoro-3-methyl-1H-indole-2-carboxamide

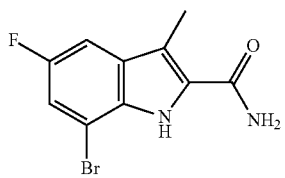

Step A (2-Bromo-4-fluoro-phenyl)-hydrazine, white solid (1.63 g, 89%), MS (ISP) m/z=205.1 [(M+H)$^+$], mp 76° C., was prepared in accordance with the general method of intermediate 3, step A, from commercially available 2-bromo-4-fluoro-aniline (1.7 g, 8.95 mmol).

Step B (Z)-2-[(2-bromo-4-fluoro-phenyl)-hydrazono]-butyric acid methyl ester (2.03 g, 85%) as an orange solid, MS (ISP) m/z=303.3 [(M+H)$^+$], mp 44° C., was prepared in accordance with the general method of intermediate 5, step B, from (2-bromo-4-fluoro-phenyl)-hydrazine (step A) (1.62 g, 7.9 mmol).

Step C

Methyl 7-bromo-5-fluoro-3-methyl-1H-indole-2-carboxylate, light yellow solid (1.62 g, 85%), MS (ISN) m/z=286.3 [(M−H)$^-$], mp 127° C., was prepared in accordance with the general method of intermediate 5, step C, from (Z)-2-[(2-bromo-4-fluoro-phenyl)-hydrazono]-butyric acid methyl ester (step B) (2.02 g, 6.66 mmol).

Step D

7-Bromo-5-fluoro-3-methyl-1H-indole-2-carboxylic acid, brown solid (0.73 g, 96%), MS (ISN) m/z=272.1 [(M−H)$^-$], mp 265° C., was prepared in accordance with the general method of intermediate 1, step B, from methyl 7-bromo-5-fluoro-3-methyl-1H-indole-2-carboxylate (step C) (0.8 g, 2.8 mmol).

Step E

The title compound, grey solid (613 mg, 84%), MS (ISP) m/z=271.3 [(M+H)$^+$], mp 273° C., was prepared in accordance with the general method of intermediate 1, step C, from 7-bromo-5-cyano-1-methylindole-2-carboxylic acid (step D) (0.73 g, 2.68 mmol).

Intermediate 10

7-Bromo-5-fluoro-1,3-dimethylindole-2-carboxamide

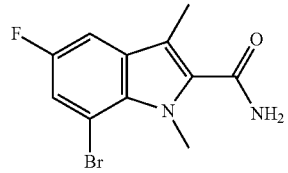 [SMILES: Cc1c(C(N)=O)n(C)c2c(Br)cc(F)cc12]

Step A

Methyl 7-bromo-5-fluoro-1,3-dimethylindole-2-carboxylate, light yellow solid (0.75 g, 89%), MS (ISP) m/z=302.3 [(M+H)$^+$], mp 76° C., was prepared in accordance with the general method of intermediate 1, step A, from methyl 7-bromo-5-fluoro-3-methyl-1H-indole-2-carboxylate (intermediate 9, step C) (0.8 g, 2.8 mmol).

Step B

7-Bromo-5-fluoro-1,3-dimethylindole-2-carboxylic acid, white solid (687 mg, 97%), MS (ISP) m/z=286.4 [(M+H)$^+$], mp 225° C., was prepared in accordance with the general method of intermediate 1, step B, from methyl 7-bromo-5-fluoro-1,3-dimethylindole-2-carboxylate (step A) (0.74 g, 2.47 mmol).

Step C

The title compound, white solid (628 mg, 92%), MS (ISP) m/z=287.3 [(M+H)$^+$], mp 248° C., was prepared in accordance with the general method of intermediate 1, step C, from 7-bromo-5-fluoro-1,3-dimethylindole-2-carboxylic acid (step B) (687 mg, 2.4 mmol).

EXAMPLE 1

7-(4-Chloro-phenyl)-5-cyano-1,3-dimethylindole-2-carboxamide

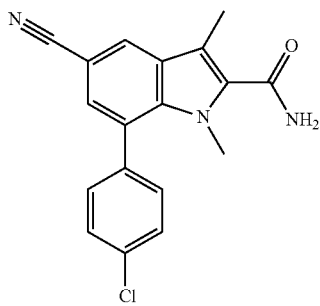 [SMILES: Cc1c(C(N)=O)n(C)c2c(-c3ccc(Cl)cc3)cc(C#N)cc12]

To a stirred solution of 7-bromo-5-cyano-1,3-dimethylindole-2-carboxamide (Intermediate 4) (98 mg, 335 mol) and commercially available 4-chlorophenylboronic acid (68.2 mg, 436 mol) in 1,2-dimethoxyethane (2.3 ml) was added at room temperature 2M sodium carbonate solution (559 µl, 1.12 mmol), and afterwards the reaction mixture was purged with argon in an ultrasonic bath over a period of 5 min. Afterwards triphenylphosphine (17.6 mg, 67.1 mol) and palladium(II)acetate (7.53 mg, 33.5 µmol) were added, and the reaction mixture was allowed to stir for stirred 2 h under reflux conditions. The reaction mixture was cooled to room temperature, filtered over MgSO$_4$ and purified by flash chromatography on silica gel (dichloromethane/MeOH 0-5%) crystallization from dichloromethane/heptane to yield the title compound as a grey solid (90 mg, 83%), MS (ISN) m/z=324.5 [(M+H)$^+$], mp 237° C.

EXAMPLE 2

5-Fluoro-7-(4-fluoro-phenyl)-1-methylindole-2-carboxamide

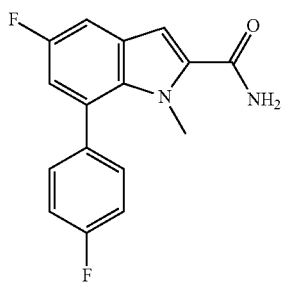 [SMILES: Cn1c(C(N)=O)cc2cc(F)cc(-c3ccc(F)cc3)c21]

The title compound, brown solid (117 mg, 92%), MS (ISP) m/z=287.5 [(M+H)$^+$], mp 156° C., was prepared in accordance with the general method of example 1 from 7-bromo-5-fluoro-1-methylindole-2-carboxylic acid amide (intermediate 1) (120 mg, 0.443 mmol) and commercially available 4-fluoro-phenylboronic acid (80.5 mg, 0.575 mmol).

EXAMPLE 3

5-Fluoro-7-(4-fluoro-phenyl)-1H-indole-2-carboxamide

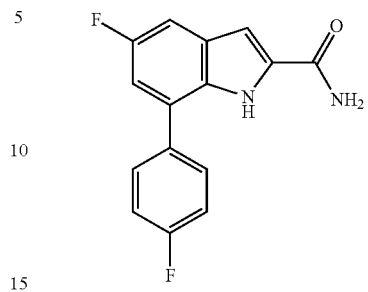

The title compound, light brown solid (117 mg, 92%), MS (ISP) m/z=273.5 [(M+H)$^+$], mp 162° C., was prepared in accordance with the general method of example 1 from 7-bromo-5-fluoro-1H-indole-2-carboxylic acid amide (intermediate 2) (120 mg, 0.467 mmol) and commercially available 4-fluoro-phenylboronic acid (84.9 mg, 0.607 mmol).

EXAMPLE 4

5-Cyano-7-(4-fluorophenyl)-1,3-dimethylindole-2-carboxamide

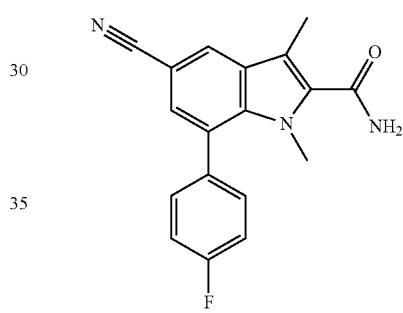

The title compound, white solid (63 mg, 82%), MS (ISP) m/z=308.5 [(M+H)$^+$], mp 216° C., was prepared in accordance with the general method of example 1 from 7-bromo-5-cyano-1,3-dimethylindole-2-carboxamide (Intermediate 4) (73 mg, 250 µmol) and commercially available 4-fluoro-phenylboronic acid (45.5 mg, 0.325 mmol).

EXAMPLE 5

5-Cyano-7-(3,4-difluorophenyl)-1,3-dimethylindole-2-carboxamide

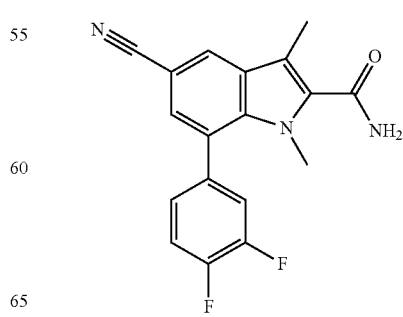

The title compound, light grey solid (62 mg, 76%), MS (ISP) m/z=326.5 [(M+H)⁺], mp 212° C., was prepared in accordance with the general method of example 1 from 7-bromo-5-cyano-1,3-dimethylindole-2-carboxamide (Intermediate 4) (73 mg, 250 µmol) and commercially available 3,4-difluoro-phenylboronic acid (51.3 mg, 0.325 mmol).

EXAMPLE 6

5-Cyano-1,3-dimethyl-7-[4-(trifluoromethyl)-phenyl]-indole-2-carboxamide

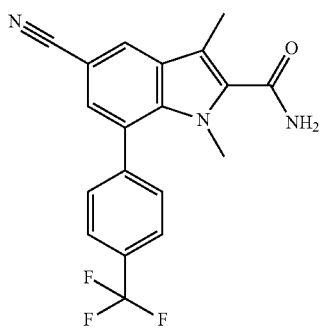

The title compound, light yellow solid (74 mg, 83%), MS (ISP) m/z=358.5 [(M+H)⁺], mp 195° C., was prepared in accordance with the general method of example 1 from 7-bromo-5-cyano-1,3-dimethylindole-2-carboxamide (Intermediate 4) (73 mg, 250 µmol) and commercially available 4-trifluoromethyl-phenylboronic acid (61.7 mg, 0.325 mmol).

EXAMPLE 7

5-Cyano-7-(3,4-difluorophenyl)-3-methyl-1H-indole-2-carboxamide

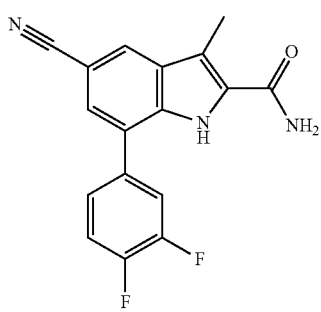 [SMILES: Cc1c(C(N)=O)[nH]c2c(-c3ccc(F)c(F)c3)cc(C#N)cc12]

The title compound, light brown solid (66 mg, 85%), MS (ISP) m/z=312.5 [(M+H)⁺], mp 222° C., was prepared in accordance with the general method of example 1 from 7-bromo-5-cyano-3-methyl-1H-indole-2-carboxamide (Intermediate 3) (69.5 mg, 250 mol) and commercially available 3,4-difluoro-phenylboronic acid (51.3 mg, 0.325 mmol).

EXAMPLE 8

5-Cyano-3-methyl-7-[4-(trifluoromethyl)phenyl]-1H-indole-2-carboxamide

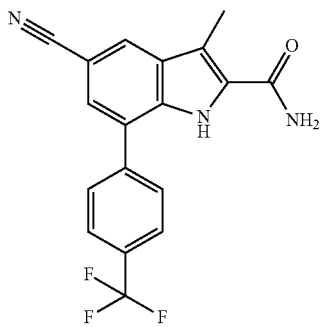 [SMILES: Cc1c(C(N)=O)[nH]c2c(-c3ccc(C(F)(F)F)cc3)cc(C#N)cc12]

The title compound, light brown solid (67 mg, 78%), MS (ISP) m/z=344.5 [(M+H)⁺], mp 243° C., was prepared in accordance with the general method of example 1 from 7-bromo-5-cyano-3-methyl-1H-indole-2-carboxamide (Intermediate 3) (69.5 mg, 250 mol) and commercially available 4-trifluoromethyl-phenylboronic acid (61.7 mg, 0.325 mmol).

EXAMPLE 9

5-Cyano-7-(4-fluorophenyl)-3-methyl-1H-indole-2-carboxamide

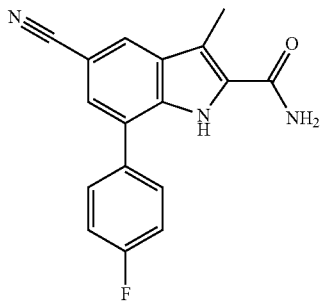

The title compound, light brown solid (57 mg, 78%), MS (ISP) m/z=292.4 [(M+H)⁺], mp 268° C., was prepared in accordance with the general method of example 1 from 7-bromo-5-cyano-3-methyl-1H-indole-2-carboxamide (Intermediate 3) (69.5 mg, 250 mol) and commercially available 4-fluoro-phenylboronic acid (45.5 mg, 0.325 mmol).

EXAMPLE 10

7-(4-Chlorophenyl)-5-cyano-3-methyl-1H-indole-2-carboxamide

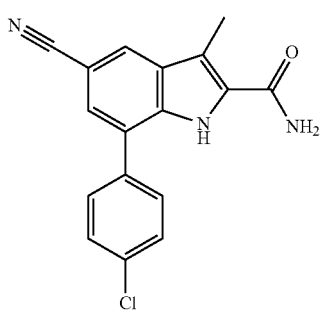 [SMILES: Cc1c(C(N)=O)[nH]c2c(-c3ccc(Cl)cc3)cc(C#N)cc12]

The title compound, light brown solid (66 mg, 85%), MS (ISP) m/z=308.4 [(M+H)+], mp 291° C., was prepared in accordance with the general method of example 1 from 7-bromo-5-cyano-3-methyl-1H-indole-2-carboxamide (Intermediate 3) (69.5 mg, 250 µmol) and commercially available 4-chloro-phenylboronic acid (50.8 mg, 0.325 mmol).

EXAMPLE 11

5-Chloro-7-(4-fluorophenyl)-3-methyl-1H-indole-2-carboxamide

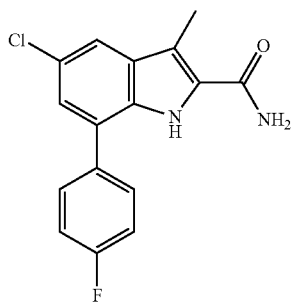

The title compound, off-white solid (62 mg, 82%), MS (ISP) m/z=301.5 [(M+H)+], mp 173° C., was prepared in accordance with the general method of example 1 from 7-bromo-5-chloro-3-methyl-1H-indole-2-carboxamide (Intermediate 5) (71.9 mg, 250 µmol) and commercially available 4-fluoro-phenylboronic acid (45.5 mg, 0.325 mmol).

EXAMPLE 12

5-Chloro-7-(4-chlorophenyl)-3-methyl-1H-indole-2-carboxamide

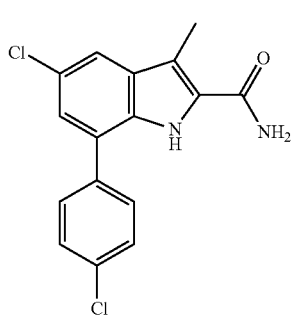 [SMILES: Cc1c(C(N)=O)[nH]c2c(-c3ccc(Cl)cc3)cc(Cl)cc12]

The title compound, off-white solid (63 mg, 79%), MS (ISP) m/z=317.5 [(M+H)+], mp 252° C., was prepared in accordance with the general method of example 1 from 7-bromo-5-chloro-3-methyl-1H-indole-2-carboxamide (Intermediate 5) (71.9 mg, 250 µmol) and commercially available 4-chloro-phenylboronic acid (50.8 mg, 0.325 mmol).

EXAMPLE 13

5-Chloro-7-(4-fluorophenyl)-1,3-dimethylindole-2-carboxamide

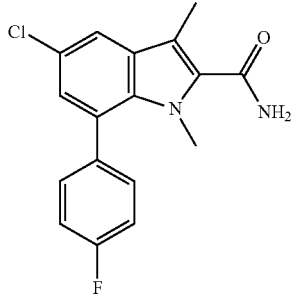

The title compound, off-white solid (63 mg, 80%), MS (ISP) m/z=317.5 [(M+H)+], mp 178° C., was prepared in accordance with the general method of example 1 from 7-bromo-5-chloro-1,3-dimethylindole-2-carboxamide (Intermediate 6) (75.4 mg, 250 mol) and commercially available 4-fluoro-phenylboronic acid (45.5 mg, 0.325 mmol).

EXAMPLE 14

5-Chloro-7-(4-chlorophenyl)-1,3-dimethylindole-2-carboxamide

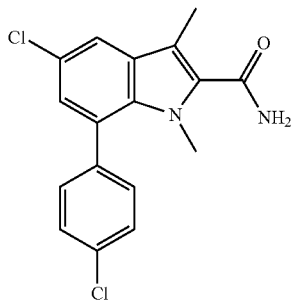 [SMILES: Cc1c(C(N)=O)n(C)c2c(-c3ccc(Cl)cc3)cc(Cl)cc12]

The title compound, off-white solid (66 mg, 79%), MS (ISP) m/z=333.5 [(M+H)+], mp 195° C., was prepared in accordance with the general method of example 1 from 7-bromo-5-chloro-1,3-dimethylindole-2-carboxamide (Intermediate 6) (75.4 mg, 250 mol) and commercially available 4-chloro-phenylboronic acid (50.8 mg, 0.325 mmol).

EXAMPLE 15

5-Chloro-7-(3,4-difluorophenyl)-3-methyl-1H-indole-2-carboxamide

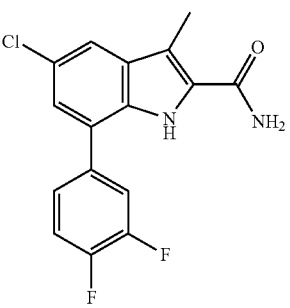 [SMILES: Cc1c(C(N)=O)[nH]c2c(-c3ccc(F)c(F)c3)cc(Cl)cc12]

The title compound, light brown solid (64 mg, 80%), MS (ISP) m/z=321.4 [(M+H)⁺], mp 206° C., was prepared in accordance with the general method of example 1 from 7-bromo-5-chloro-3-methyl-1H-indole-2-carboxamide (Intermediate 5) (71.9 mg, 250 mol) and commercially available 3,4-difluoro-phenylboronic acid (51.3 mg, 0.325 mmol).

EXAMPLE 16

5-Chloro-3-methyl-7-[4-(trifluoromethyl)-phenyl]-1H-indole-2-carboxamide

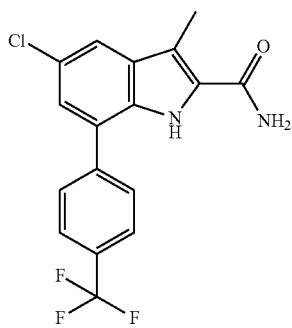 [SMILES: Cc1c(C(N)=O)[nH]c2c(-c3ccc(C(F)(F)F)cc3)cc(Cl)cc12]

The title compound, off-white solid (62 mg, 70%), MS (ISP) m/z=353.4 [(M+H)⁺], mp 184° C., was prepared in accordance with the general method of example 1 from 7-bromo-5-chloro-3-methyl-1H-indole-2-carboxamide (Intermediate 5) (71.9 mg, 250 mol) and commercially available 4-trifluoromethyl-phenylboronic acid (61.7 mg, 0.325 mmol).

EXAMPLE 17

5-Chloro-7-(3,4-difluorophenyl)-1,3-dimethylindole-2-carboxamide

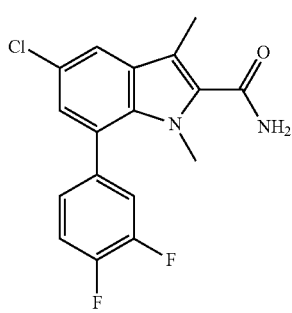

The title compound, off-white solid (56 mg, 67%), MS (ISP) m/z=335.4 [(M+H)⁺], mp 196° C., was prepared in accordance with the general method of example 1 from 7-bromo-5-chloro-1,3-dimethylindole-2-carboxamide (Intermediate 6) (75.4 mg, 250 mol) and commercially available 3,4-difluoro-phenylboronic acid (51.3 mg, 0.325 mmol).

EXAMPLE 18

5-Chloro-1,3-dimethyl-7-[4-(trifluoromethyl)phenyl]indole-2-carboxamide

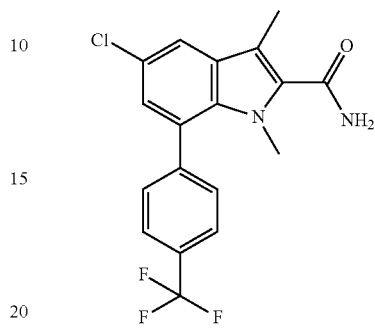

The title compound, white solid (59 mg, 64%), MS (ISP) m/z=367.4 [(M+H)⁺], mp 206° C., was prepared in accordance with the general method of example 1 from 7-bromo-5-chloro-1,3-dimethylindole-2-carboxamide (Intermediate 6) (75.4 mg, 250 µmol) and commercially available 4-trifluoromethyl-phenylboronic acid (61.7 mg, 0.325 mmol).

EXAMPLE 19

5-Cyano-3-methyl-7-[4-(trifluoromethoxy)-phenyl]-1H-indole-2-carboxamide

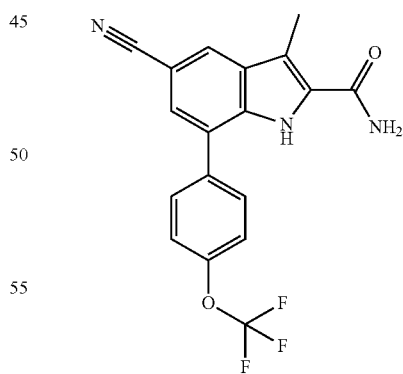

The title compound, light brown solid (36 mg, 40%), MS (ISP) m/z=360.4 [(M+H)⁺], mp 207° C., was prepared in accordance with the general method of example 1 from 7-bromo-5-cyano-3-methyl-1H-indole-2-carboxamide (Intermediate 3) (69.5 mg, 250 mol) and commercially available 4-trifluoromethoxy-phenylboronic acid (66.9 mg, 0.325 mmol).

EXAMPLE 20

5-Cyano-7-(4-cyanophenyl)-3-methyl-1H-indole-2-carboxamide

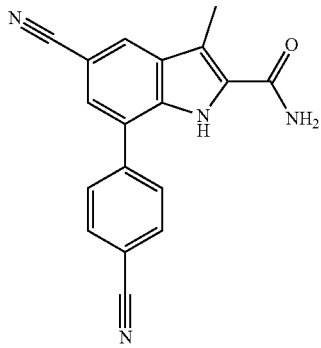 [SMILES: Cc1c(C(N)=O)[nH]c2c(-c3ccc(C#N)cc3)cc(C#N)cc12]

The title compound, light yellow solid (54 mg, 72%), MS (ISP) m/z=299.4 [(M+H)$^+$], mp 294° C., was prepared in accordance with the general method of example 1 from 7-bromo-5-cyano-3-methyl-1H-indole-2-carboxamide (Intermediate 3) (69.5 mg, 250 mol) and commercially available 4-cyanophenylboronic acid (47.8 mg, 0.325 mmol).

EXAMPLE 21

5-Cyano-1,3-dimethyl-7-[4-(trifluoromethoxy)phenyl]indole-2-carboxamide

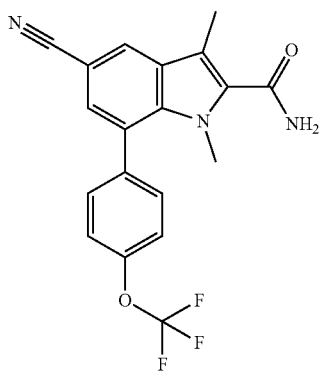 [SMILES: Cc1c(C(N)=O)n(C)c2c(-c3ccc(OC(F)(F)F)cc3)cc(C#N)cc12]

The title compound, off-white solid (75 mg, 80%), MS (ISP) m/z=374.4 [(M+H)$^+$], mp 106° C., was prepared in accordance with the general method of example 1 from 7-bromo-5-cyano-1,3-dimethylindole-2-carboxamide (Intermediate 4) (73 mg, 250 μmol) and commercially available 4-trifluoromethoxy-phenylboronic acid (66.9 mg, 0.325 mmol).

EXAMPLE 22

5-Cyano-7-(4-cyanophenyl)-1,3-dimethylindole-2-carboxamide

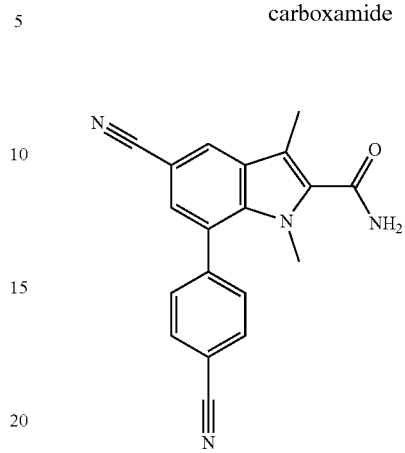

The title compound, off-white solid (60 mg, 76%), MS (ISP) m/z=315.4 [(M+H)$^+$], mp 226° C., was prepared in accordance with the general method of example 1 from 7-bromo-5-cyano-1,3-dimethylindole-2-carboxamide (Intermediate 4) (73 mg, 250 μmol) and commercially available 4-cyanophenylboronic acid (47.8 mg, 0.325 mmol).

EXAMPLE 23

5-Chloro-7-4-cyanophenyl)-3-methyl-1H-indole-2-carboxamide

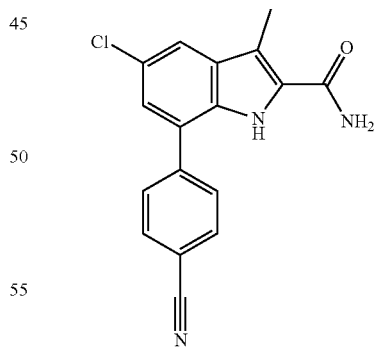

The title compound, off-white solid (60 mg, 78%), MS (ISP) m/z=310.4 [(M+H)$^+$], mp 267° C., was prepared in accordance with the general method of example 1 from 7-bromo-5-chloro-3-methyl-1H-indole-2-carboxamide (Intermediate 5) (71.9 mg, 250 μmol) and commercially available 4-cyanophenylboronic acid (47.8 mg, 0.325 mmol).

EXAMPLE 24

5-Chloro-3-methyl-7-[4-(trifluoromethoxy)phenyl]-1H-indole-2-carboxamide

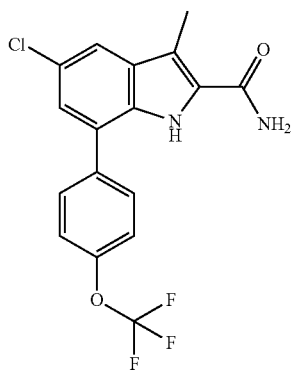 [SMILES: Cc1c(C(N)=O)[nH]c2c(-c3ccc(OC(F)(F)F)cc3)cc(Cl)cc12]

The title compound, off-white solid (57 mg, 62%), MS (ISP) m/z=369.4 [(M+H)⁺], mp 149° C., was prepared in accordance with the general method of example 1 from 7-bromo-5-chloro-3-methyl-1H-indole-2-carboxamide (Intermediate 5) (71.9 mg, 250 µmol) and commercially available 4-trifluoromethoxy-phenylboronic acid (66.9 mg, 0.325 mmol).

EXAMPLE 25

5-Chloro-7-(2,4-difluorophenyl)-3-methyl-1H-indole-2-carboxamide

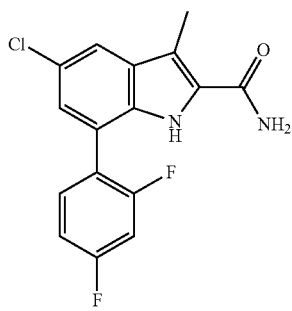 [SMILES: Cc1c(C(N)=O)[nH]c2c(-c3ccc(F)cc3F)cc(Cl)cc12]

The title compound, off-white solid (70 mg, 87%), MS (ISP) m/z=321.4 [(M+H)⁺], mp 196° C., was prepared in accordance with the general method of example 1 from 7-bromo-5-chloro-3-methyl-1H-indole-2-carboxamide (Intermediate 5) (71.9 mg, 250 µmol) and commercially available 2,4-difluoro-phenylboronic acid (51.3 mg, 0.325 mmol).

EXAMPLE 26

5-Chloro-7-(2,4-dichlorophenyl)-3-methyl-1H-indole-2-carboxamide

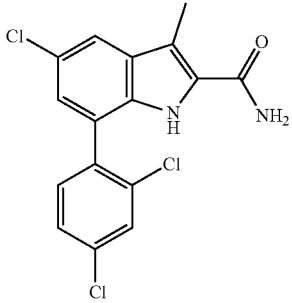 [SMILES: Cc1c(C(N)=O)[nH]c2c(-c3ccc(Cl)cc3Cl)cc(Cl)cc12]

The title compound, yellow solid (65 mg, 74%), MS (ISP) m/z=353.3 [(M+H)⁺], mp 195° C., was prepared in accordance with the general method of example 1 from 7-bromo-5-chloro-3-methyl-1H-indole-2-carboxamide (Intermediate 5) (71.9 mg, 250 µmol) and commercially available 2,4-dichloro-phenylboronic acid (62.0 mg, 0.325 mmol).

EXAMPLE 27

5-Chloro-1,3-dimethyl-7-[4-(trifluoromethoxy)-phenyl]indole-2-carboxamide

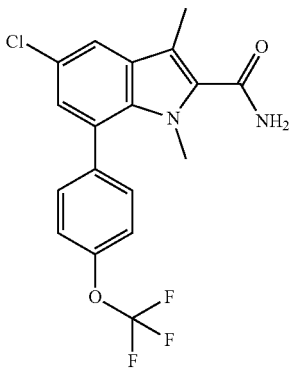 [SMILES: Cc1c(C(N)=O)n(C)c2c(-c3ccc(OC(F)(F)F)cc3)cc(Cl)cc12]

The title compound, off-white solid (60 mg, 63%), MS (ISP) m/z=383.4 [(M+H)⁺], mp 181° C., was prepared in accordance with the general method of example 1 from 7-bromo-5-chloro-1,3-dimethylindole-2-carboxamide (Intermediate 6) (75.4 mg, 250 µmol) and commercially available 4-trifluoromethoxy-phenylboronic acid (66.9 mg, 0.325 mmol).

EXAMPLE 28

5-Chloro-7-(4-cyanophenyl)-1,3-dimethylindole-2-carboxamide

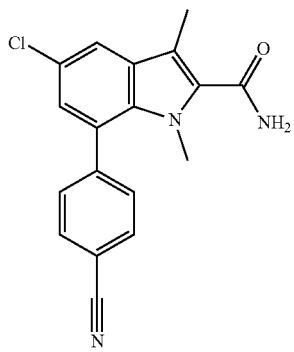 [SMILES: Cc1c(C(N)=O)n(C)c2c(-c3ccc(C#N)cc3)cc(Cl)cc12]

The title compound, off-white solid (67 mg, 83%), MS (ISP) m/z=324.4 [(M+H)+], mp 199° C., was prepared in accordance with the general method of example 1 from 7-bromo-5-chloro-1,3-dimethylindole-2-carboxamide (Intermediate 6) (75.4 mg, 250 µmol) and commercially available 4-cyanophenylboronic acid (47.8 mg, 0.325 mmol).

EXAMPLE 29

5-Chloro-7-(2,4-difluorophenyl)-1,3-dimethylindole-2-carboxamide

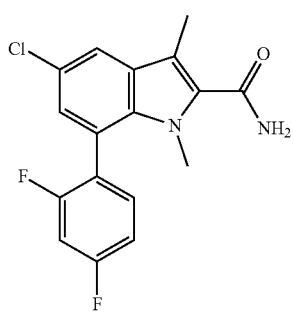 [SMILES: Cc1c(C(N)=O)n(C)c2c(-c3ccc(F)cc3F)cc(Cl)cc12]

The title compound, white solid (27 mg, 32%), MS (ISP) m/z=335.4 [(M+H)+], mp 220° C., was prepared in accordance with the general method of example 1 from 7-bromo-5-chloro-1,3-dimethylindole-2-carboxamide (Intermediate 6) (75.4 mg, 250 µmol) and commercially available 2,4-difluoro-phenylboronic acid (51.3 mg, 0.325 mmol).

EXAMPLE 30

5-Chloro-7-(2,4-dichlorophenyl)-1,3-dimethylindole-2-carboxamide

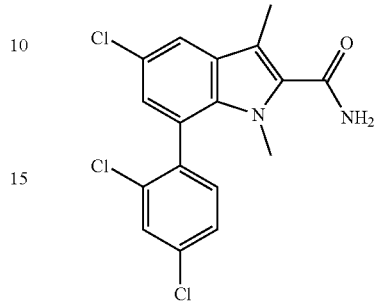

The title compound, white solid (62 mg, 67%), MS (ISP) m/z=367.3 [(M+H)+], mp 221° C., was prepared in accordance with the general method of example 1 from 7-bromo-5-chloro-1,3-dimethylindole-2-carboxamide (Intermediate 6) (75.4 mg, 250 µmol) and commercially available 2,4-dichloro-phenylboronic acid (62.0 mg, 0.325 mmol).

EXAMPLE 31

5-Chloro-7-(4-chloro-3-fluorophenyl)-3-methyl-1H-indole-2-carboxamide

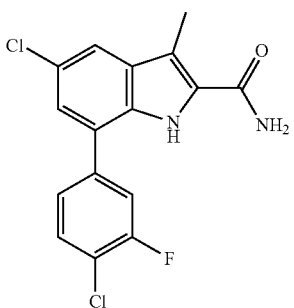 [SMILES: Cc1c(C(N)=O)[nH]c2c(-c3ccc(Cl)c(F)c3)cc(Cl)cc12]

The title compound, off-white solid (50 mg, 59%), MS (ISP) m/z=335.3 [(M+H)+], mp 283° C., was prepared in accordance with the general method of example 1 from 7-bromo-5-chloro-3-methyl-1H-indole-2-carboxamide (Intermediate 5) (71.9 mg, 250 µmol) and commercially available 4-chloro-3-fluoro-phenylboronic acid (56.7 mg, 0.325 mmol).

EXAMPLE 32

5-Chloro-7-(4-chloro-3-fluorophenyl)-1,3-dimethyl-indole-2-carboxamide

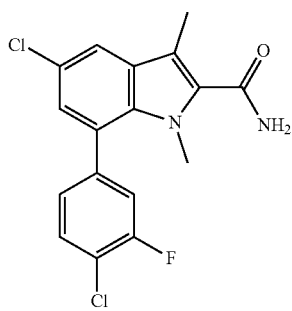 [SMILES: Cc1c(C(N)=O)n(C)c2c(-c3ccc(Cl)c(F)c3)cc(Cl)cc12]

The title compound, off-white solid (68 mg, 77%), MS (ISP) m/z=351.4 [(M+H)$^+$], mp 192° C., was prepared in accordance with the general method of example 1 from 7-bromo-5-chloro-1,3-dimethylindole-2-carboxamide (Intermediate 6) (75.4 mg, 250 µmol) and commercially available 4-chloro-3-fluoro-phenylboronic acid (56.7 mg, 0.325 mmol).

EXAMPLE 33

5-Cyano-7-3,4-difluorophenyl)-1H-indole-2-carboxamide

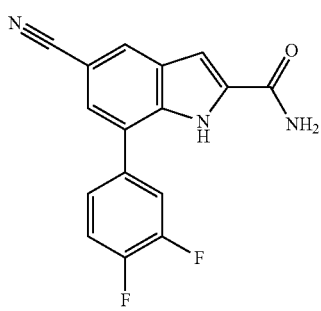

The title compound, light grey solid (53 mg, 71%), MS (ISP) m/z=335.4 [(M+H)$^+$], mp 262° C., was prepared in accordance with the general method of example 1 from 7-bromo-5-cyano-1H-indole-2-carboxamide (Intermediate 7) (66 mg, 250 µmol) and commercially available 3,4-difluoro-phenylboronic acid (51.3 mg, 0.325 mmol).

EXAMPLE 34

5-Cyano-7-(4-fluorophenyl)-1H-indole-2-carboxamide

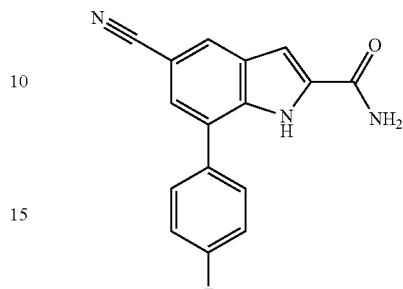

The title compound, light grey solid (52 mg, 75%), MS (ISP) m/z=280.1 [(M+H)$^+$], mp 234° C., was prepared in accordance with the general method of example 1 from 7-bromo-5-cyano-1H-indole-2-carboxamide (Intermediate 7) (66 mg, 250 µmol) and commercially available 4-fluoro-phenylboronic acid (45.5 mg, 0.325 mmol).

EXAMPLE 35

7-(4-Chlorophenyl)-5-cyano-1H-indole-2-carboxamide

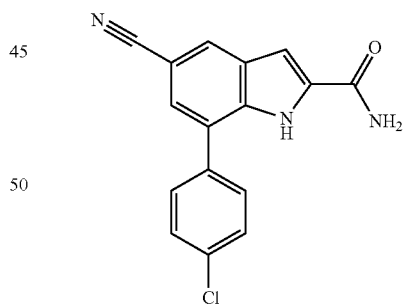

The title compound, off-white solid (58 mg, 79%), MS (ISP) m/z=296.0 [(M+H)$^+$], mp 267.5° C., was prepared in accordance with the general method of example 1 from 7-bromo-5-cyano-1H-indole-2-carboxamide (Intermediate 7) (66 mg, 250 µmol) and commercially available 4-chloro-phenylboronic acid (50.8 mg, 0.325 mmol).

EXAMPLE 36

5-Cyano-7-[4-(trifluoromethyl)phenyl]-1H-indole-2-carboxamide

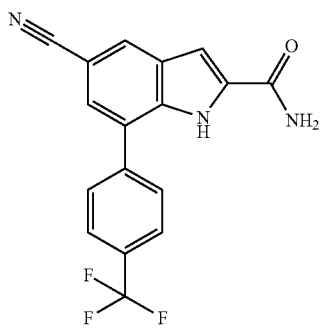 [SMILES: N#Cc1cc(-c2ccc(C(F)(F)F)cc2)c2[nH]c(C(N)=O)cc2c1]

The title compound, off-white solid (60 mg, 73%), MS (ISP) m/z=330.4 [(M+H)$^+$], mp 277.5° C., was prepared in accordance with the general method of example 1 from 7-bromo-5-cyano-1H-indole-2-carboxamide (Intermediate 7) (66 mg, 250 μmol) and commercially available 4-trifluoromethyl-phenylboronic acid (61.7 mg, 0.325 mmol).

EXAMPLE 37

5-Cyano-1-methyl-7-[4-(trifluoromethyl)-phenyl]-indole-2-carboxamide

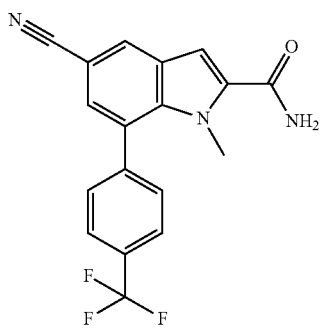 [SMILES: Cn1c(C(N)=O)cc2cc(C#N)cc(-c3ccc(C(F)(F)F)cc3)c21]

The title compound, off-white solid (68 mg, 79%), MS (ISP) m/z=344.5 [(M+H)$^+$], mp 171° C., was prepared in accordance with the general method of example 1 from 7-bromo-5-cyano-1-methylindole-2-carboxamide (Intermediate 8) (69.5 mg, 250 μmol) and commercially available 4-trifluoromethyl-phenylboronic acid (61.7 mg, 0.325 mmol).

EXAMPLE 38

5-Cyano-7-(4-fluorophenyl)-1-methylindole-2-carboxamide

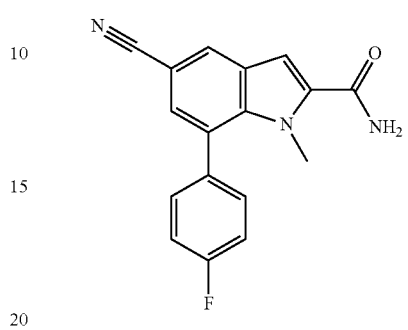

The title compound, grey solid (60 mg, 82%), MS (ISP) m/z=294.4 [(M+H)$^+$], mp 203.5° C., was prepared in accordance with the general method of example 1 from 7-bromo-5-cyano-1-methylindole-2-carboxamide (Intermediate 8) (69.5 mg, 250 μmol) and commercially available 4-fluorophenylboronic acid (45.5 mg, 0.325 mmol).

EXAMPLE 39

7-(4-Chlorophenyl)-5-cyano-1-methylindole-2-carboxamide

The title compound, white solid (63 mg, 81%), MS (ISP) m/z=310.4 [(M+H)$^+$], mp 176° C., was prepared in accordance with the general method of example 1 from 7-bromo-5-cyano-1-methylindole-2-carboxamide (Intermediate 8) (69.5 mg, 250 μmol) and commercially available 4-chlorophenylboronic acid (50.8 mg, 0.325 mmol).

EXAMPLE 40

5-Cyano-7-(3,4-difluorophenyl)-1-methylindole-2-carboxamide

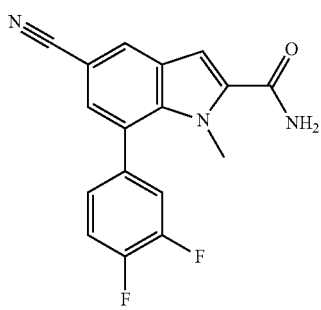 [SMILES: Cn1c(C(N)=O)cc2cc(C#N)cc(-c3ccc(F)c(F)c3)c21]

The title compound, off-white solid (58 mg, 75%), MS (ISP) m/z=312.5 [(M+H)⁺], mp 184.5° C., was prepared in accordance with the general method of example 1 from 7-bromo-5-cyano-1-methylindole-2-carboxamide (Intermediate 8) (69.5 mg, 250 mol) and commercially available 3,4-difluoro-phenylboronic acid (51.3 mg, 0.325 mmol).

EXAMPLE 41

5-Cyano-7-(2,4-difluorophenyl)-1H-indole-2-carboxamide

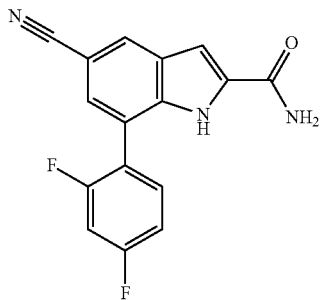 [SMILES: N#Cc1cc(-c2ccc(F)cc2F)c2[nH]c(C(N)=O)cc2c1]

The title compound, light brown solid (50 mg, 67%), MS (ISP) m/z=298.5 [(M+H)⁺], mp 289.5° C., was prepared in accordance with the general method of example 1 from 7-bromo-5-cyano-1H-indole-2-carboxamide (Intermediate 7) (66 mg, 250 mol) and commercially available 2,4-difluoro-phenylboronic acid (51.3 mg, 0.325 mmol).

EXAMPLE 42

5-Cyano-7-(2,4-dichlorophenyl)-1H-indole-2-carboxamide

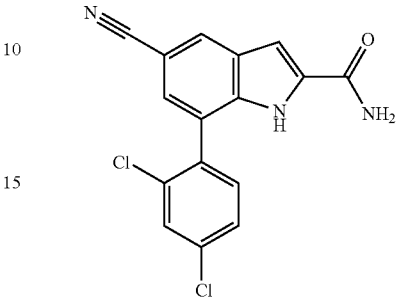

The title compound, light yellow solid (59 mg, 72%), MS (ISP) m/z=330.4 [(M+H)⁺], mp 276.5° C., was prepared in accordance with the general method of example 1 from 7-bromo-5-cyano-1H-indole-2-carboxamide (Intermediate 7) (66 mg, 250 mol) and commercially available 2,4-dichloro-phenylboronic acid (62.0 mg, 0.325 mmol).

EXAMPLE 43

5-Cyano-7-(4-cyanophenyl)-1H-indole-2-carboxamide

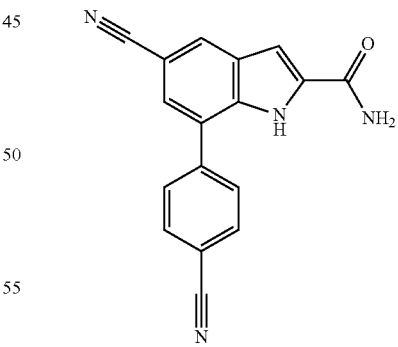

The title compound, off-white solid (35 mg, 49%), MS (ISP) m/z=287.5 [(M+H)⁺], mp 299° C., was prepared in accordance with the general method of example 1 from 7-bromo-5-cyano-1H-indole-2-carboxamide (Intermediate 7) (66 mg, 250 mol) and commercially available 4-cyano-phenylboronic acid (47.8 mg, 0.325 mmol).

EXAMPLE 44

5-Cyano-7-[4-(trifluoromethoxy)-phenyl]-1H-indole-2-carboxamide

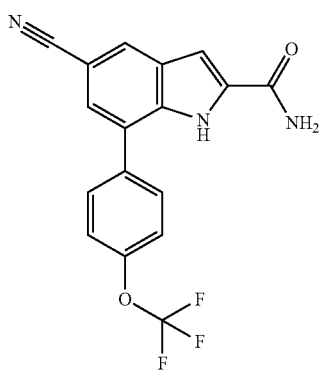 [SMILES: N#Cc1cc(-c2ccc(OC(F)(F)F)cc2)c2[nH]c(C(N)=O)cc2c1]

The title compound, light brown solid (61 mg, 71%), MS (ISP) m/z=346.4 [(M+H)+], mp 247° C., was prepared in accordance with the general method of example 1 from 7-bromo-5-cyano-1H-indole-2-carboxamide (Intermediate 7) (66 mg, 250 mol) and commercially available 4-trifluoromethoxy-phenylboronic acid (66.9 mg, 0.325 mmol).

EXAMPLE 45

5-Fluoro-7-(4-fluorophenyl)-3-methyl-1H-indole-2-carboxamide

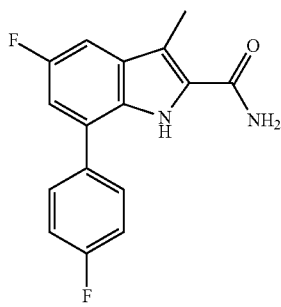 [SMILES: Cc1c(C(N)=O)[nH]c2c(-c3ccc(F)cc3)cc(F)cc12]

The title compound, white solid (43 mg, 60%), MS (ISP) m/z=287.4 [(M+H)+], mp 219° C., was prepared in accordance with the general method of example 1 from 7-bromo-5-fluoro-3-methyl-1H-indole-2-carboxamide (Intermediate 9) (67.8 mg, 250 μmol) and commercially available 4-fluoro-phenylboronic acid (45.5 mg, 0.325 mmol).

EXAMPLE 46

7-(4-Chlorophenyl)-5-fluoro-3-methyl-1H-indole-2-carboxamide

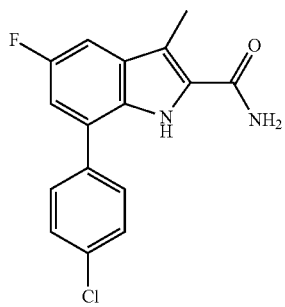

The title compound, white solid (30 mg, 40%), MS (ISP) m/z=303.4 [(M+H)+], mp 230° C., was prepared in accordance with the general method of example 1 from 7-bromo-5-fluoro-3-methyl-1H-indole-2-carboxamide (Intermediate 9) (67.8 mg, 250 μmol) and commercially available 4-chloro-phenylboronic acid (50.8 mg, 0.325 mmol).

EXAMPLE 47

7-(3,4-Difluorophenyl)-5-fluoro-3-methyl-1H-indole-2-carboxamide

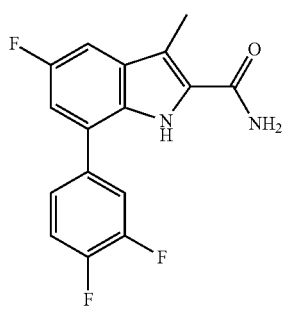

The title compound, light yellow solid (46 mg, 60%), MS (ISP) m/z=305.1 [(M+H)+], mp 208° C., was prepared in accordance with the general method of example 1 from 7-bromo-5-fluoro-3-methyl-1H-indole-2-carboxamide (Intermediate 9) (67.8 mg, 250 mol) and commercially available 3,4-difluoro-phenylboronic acid (51.3 mg, 0.325 mmol).

EXAMPLE 48

5-Fluoro-3-methyl-7-[4-(trifluoromethyl)-phenyl]-1H-indole-2-carboxamide

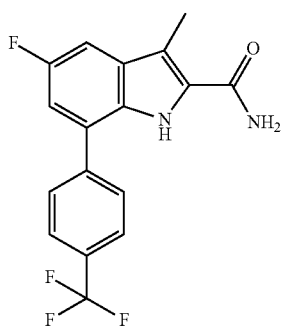 [SMILES: Cc1c(C(N)=O)[nH]c2c(-c3ccc(C(F)(F)F)cc3)cc(F)cc12]

The title compound, light brown solid (51 mg, 61%), MS (ISP) m/z=337.1 [(M+H)+], mp 200° C., was prepared in accordance with the general method of example 1 from 7-bromo-5-fluoro-3-methyl-1H-indole-2-carboxamide (Intermediate 9) (67.8 mg, 250 mol) and commercially available 4-trifluoromethyl-phenylboronic acid (61.7 mg, 0.325 mmol).

EXAMPLE 49

5-Fluoro-7-(4-fluorophenyl)-1,3-dimethylindole-2-carboxamide

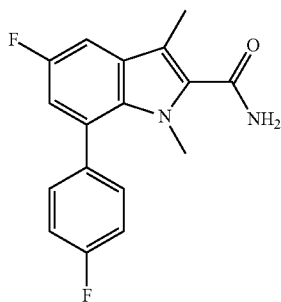 [SMILES: Cc1c(C(N)=O)n(C)c2c(-c3ccc(F)cc3)cc(F)cc12]

The title compound, light yellow solid (58 mg, 77%), MS (ISP) m/z=301.1 [(M+H)+], mp 202° C., was prepared in accordance with the general method of example 1 from 7-bromo-5-fluoro-1,3-dimethylindole-2-carboxamide (Intermediate 10) (71.3 mg, 250 mol) and commercially available 4-fluoro-phenylboronic acid (45.5 mg, 0.325 mmol).

EXAMPLE 50

7-(4-Chlorophenyl)-5-fluoro-1,3-dimethylindole-2-carboxamide

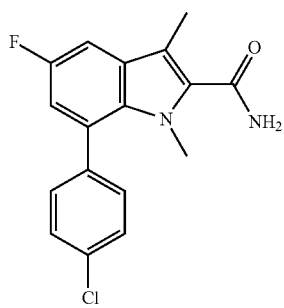

The title compound, light yellow solid (55 mg, 69%), MS (ISP) m/z=317.1 [(M+H)+], mp 210° C., was prepared in accordance with the general method of example 1 from 7-bromo-5-fluoro-1,3-dimethylindole-2-carboxamide (Intermediate 10) (71.3 mg, 250 mol) and commercially available 4-chloro-phenylboronic acid (50.8 mg, 0.325 mmol).

EXAMPLE 51

5-Fluoro-1,3-dimethyl-7-[4-(trifluoromethyl)-phenyl]-indole-2-carboxamide

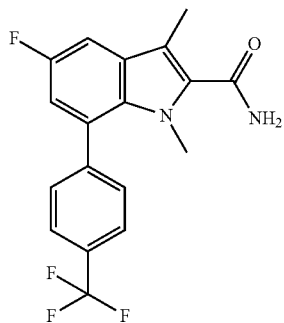 [SMILES: Cc1c(C(N)=O)n(C)c2c(-c3ccc(C(F)(F)F)cc3)cc(F)cc12]

The title compound, white solid (61 mg, 70%), MS (ISP) m/z=351.1 [(M+H)+], mp 222° C., was prepared in accordance with the general method of example 1 from 5-fluoro-1,3-dimethylindole-2-carboxamide (Intermediate 10) (71.3 mg, 250 mol) and commercially available 4-trifluoromethyl-phenylboronic acid (61.7 mg, 0.325 mmol).

EXAMPLE 52

7-(3,4-Difluorophenyl)-5-fluoro-1,3-dimethylindole-2-carboxamide

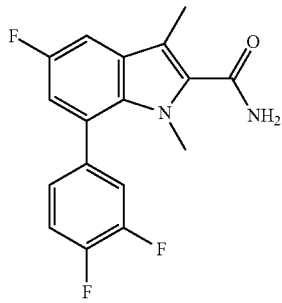 [SMILES: Cc1c(C(N)=O)n(C)c2c(-c3ccc(F)c(F)c3)cc(F)cc12]

The title compound, white solid (57 mg, 72%), MS (ISP) m/z=319.1 [(M+H)+], mp 186° C., was prepared in accordance with the general method of example 1 from 7-bromo-5-fluoro-1,3-dimethylindole-2-carboxamide (Intermediate 10) (71.3 mg, 250 mol) and commercially available 3,4-difluoro-phenylboronic acid (51.3 mg, 0.325 mmol).

EXAMPLE 53

7-(4-Cyanophenyl)-5-fluoro-3-methyl-1H-indole-2-carboxamide

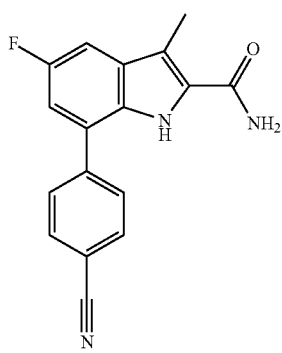

The title compound, light yellow solid (49 mg, 67%), MS (ISP) m/z=294.1 [(M+H)+], mp 230° C., was prepared in accordance with the general method of example 1 from 7-bromo-5-fluoro-3-methyl-1H-indole-2-carboxamide (Intermediate 9) (67.8 mg, 250 µmol) and commercially available 4-cyanophenylboronic acid (47.8 mg, 0.325 mmol).

EXAMPLE 54

5-Fluoro-3-methyl-7-[4-(trifluoromethoxy)phenyl]-1H-indole-2-carboxamide

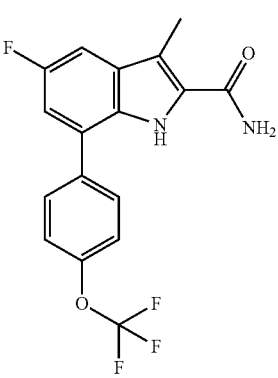

The title compound, grey solid (50 mg, 57%), MS (ISP) m/z=353.1 [(M+H)+], mp 108° C., was prepared in accordance with the general method of example 1 from 7-bromo-5-fluoro-3-methyl-1H-indole-2-carboxamide (Intermediate 9) (67.8 mg, 250 µmol) and commercially available 4-trifluoromethoxy-phenylboronic acid (66.9 mg, 0.325 mmol).

EXAMPLE 55

7-(2,4-Difluorophenyl)-5-fluoro-3-methyl-1H-indole-2-carboxamide

The title compound, white solid (35 mg, 46%), MS (ISP) m/z=305.2 [(M+H)+], mp 200° C., was prepared in accordance with the general method of example 1 from 7-bromo-5-fluoro-3-methyl-1H-indole-2-carboxamide (Intermediate 9) (67.8 mg, 250 µmol) and commercially available 2,4-difluoro-phenylboronic acid (51.3 mg, 0.325 mmol).

EXAMPLE 56

7-(2,4-Dichlorophenyl)-5-fluoro-3-methyl-1H-indole-2-carboxamide

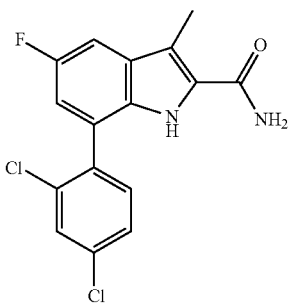 [SMILES: Cc1c(C(N)=O)[nH]c2c(-c3ccc(Cl)cc3Cl)cc(F)cc12]

The title compound, white solid (40 mg, 47%), MS (ISP) m/z=339.1 [(M+H)+], mp 198° C., was prepared in accordance with the general method of example 1 from 7-bromo-5-fluoro-3-methyl-1H-indole-2-carboxamide (Intermediate 9) (67.8 mg, 250 µmol) and commercially available 2,4-dichloro-phenylboronic acid (62.0 mg, 0.325 mmol).

EXAMPLE 57

7-(4-Chloro-2-fluorophenyl)-5-cyano-1H-indole-2-carboxamide

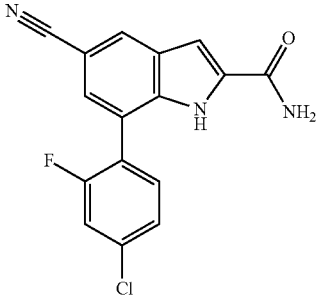

The title compound, off-white solid (51 mg, 65%), MS (ISP) m/z=314.0 [(M+H)+], mp 286.5° C., was prepared in accordance with the general method of example 1 from 7-bromo-5-cyano-1H-indole-2-carboxamide (Intermediate 7) (66 mg, 250 µmol) and commercially available 4-chloro-2-fluoro-phenylboronic acid (56.7 mg, 0.325 mmol).

EXAMPLE 58

7-(4-Chloro-2-fluorophenyl)-5-cyano-1-methylindole-2-carboxamide

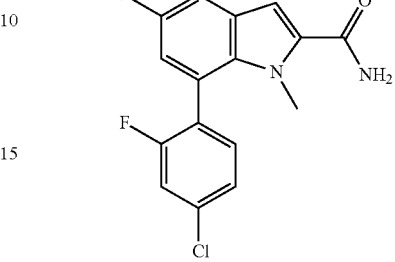

The title compound, white solid (34 mg, 42%), MS (ISP) m/z=328.1 [(M+H)+], mp 192° C., was prepared in accordance with the general method of example 1 from 7-bromo-5-cyano-1-methylindole-2-carboxamide (Intermediate 8) (69.5 mg, 250 µmol) and commercially available 4-chloro-2-fluoro-phenylboronic acid (56.7 mg, 0.325 mmol).

EXAMPLE 59

7-(4-Cyanophenyl)-5-fluoro-1,3-dimethylindole-2-carboxamide

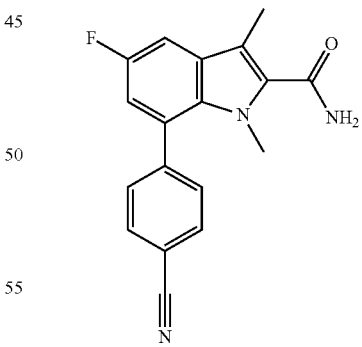

The title compound, white solid (52 mg, 68%), MS (ISP) m/z=308.2 [(M+H)+], mp 245° C., was prepared in accordance with the general method of example 1 from 7-bromo-5-fluoro-1,3-dimethylindole-2-carboxamide (Intermediate 10) (71.3 mg, 250 µmol) and commercially available 4-cyanophenylboronic acid (47.8 mg, 0.325 mmol).

EXAMPLE 60

5-Fluoro-1,3-dimethyl-7-[4-(trifluoromethoxy)phenyl]indole-2-carboxamide

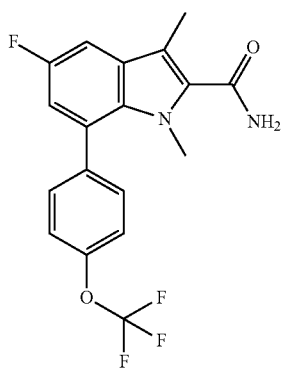 [SMILES: Cc1c(C(N)=O)n(C)c2c(-c3ccc(OC(F)(F)F)cc3)cc(F)cc12]

The title compound, light grey solid (56 mg, 61%), MS (ISP) m/z=367.2 [(M+H)+], mp 171° C., was prepared in accordance with the general method of example 1 from 7-bromo-5-fluoro-1,3-dimethylindole-2-carboxamide (Intermediate 10) (71.3 mg, 250 μmol) and commercially available 4-trifluoromethoxy-phenylboronic acid (66.9 mg, 0.325 mmol).

EXAMPLE 61

7-(2,4-Dichlorophenyl)-5-fluoro-1,3-dimethylindole-2-carboxamide

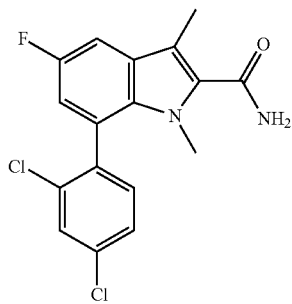 [SMILES: Cc1c(C(N)=O)n(C)c2c(-c3ccc(Cl)cc3Cl)cc(F)cc12]

The title compound, white solid (52 mg, 59%), MS (ISP) m/z=353.1 [(M+H)+], mp 169° C., was prepared in accordance with the general method of example 1 from 7-bromo-5-fluoro-1,3-dimethylindole-2-carboxamide (Intermediate 10) (71.3 mg, 250 mol) and commercially available 2,4-dichloro-phenylboronic acid (62.0 mg, 0.325 mmol).

EXAMPLE 62

5-Cyano-7-(2,4-difluorophenyl)-1-methylindole-2-carboxamide

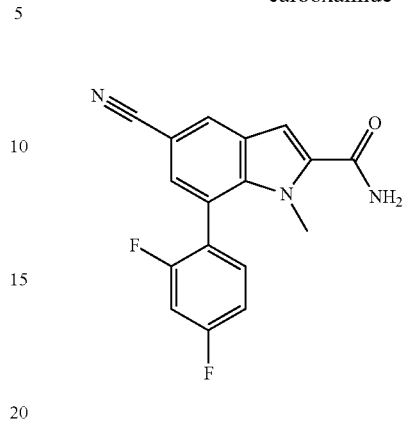

The title compound, white solid (43 mg, 55%), MS (ISP) m/z=312.1 [(M+H)+], mp 206.5° C., was prepared in accordance with the general method of example 1 from 7-bromo-5-cyano-1-methylindole-2-carboxamide (Intermediate 8) (69.5 mg, 250 μmol) and commercially available 2,4-difluoro-phenylboronic acid (51.3 mg, 0.325 mmol).

EXAMPLE 63

5-Cyano-7-(2,4-dichlorophenyl)-1-methylindole-2-carboxamide

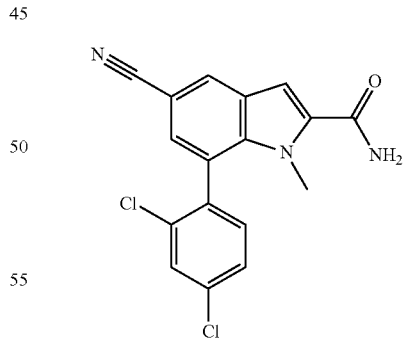

The title compound, white solid (39 mg, 45%), MS (ISP) m/z=344.1 [(M+H)+], mp 222.5° C., was prepared in accordance with the general method of example 1 from 7-bromo-5-cyano-1-methylindole-2-carboxamide (Intermediate 8) (69.5 mg, 250 μmol) and commercially available 2,4-dichloro-phenylboronic acid (62.0 mg, 0.325 mmol).

EXAMPLE 64

7-(2,4-Difluorophenyl)-5-fluoro-1,3-dimethylindole-2-carboxamide

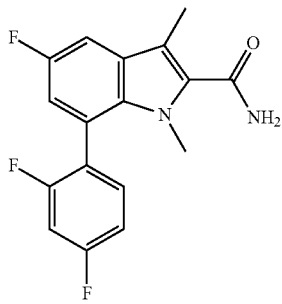

The title compound, white solid (16 mg, 20%), MS (ISP) m/z=319.1 [(M+H)$^+$], mp 192° C., was prepared in accordance with the general method of example 1 from 7-bromo-5-fluoro-1,3-dimethylindole-2-carboxamide (Intermediate 10) (71.3 mg, 250 mol) and commercially available 2,4-difluoro-phenylboronic acid (51.3 mg, 0.325 mmol).

EXAMPLE 65

5-Cyano-7-(4-fluoro-3-methylphenyl)-1-methylindole-2-carboxamide

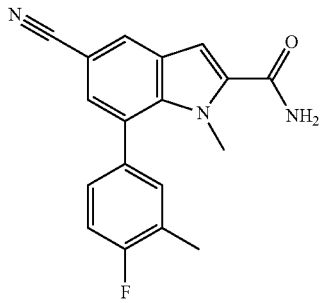

The title compound, white solid (56 mg, 73%), MS (ISP) m/z=308.1 [(M+H)$^+$], mp 220° C., was prepared in accordance with the general method of example 1 from 7-bromo-5-cyano-1-methylindole-2-carboxamide (Intermediate 8) (69.5 mg, 250 µmol) and commercially available 4-fluoro-3-methyl-phenylboronic acid (50.0 mg, 0.325 mmol).

EXAMPLE 66

5-Cyano-7-(4-fluoro-3-methylphenyl)-1H-indole-2-carboxamide

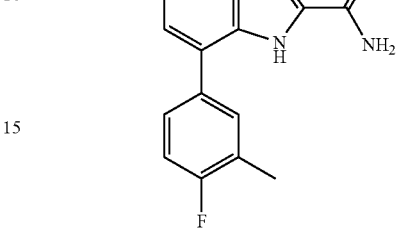

The title compound, light brown solid (53 mg, 72%), MS (ISP) m/z=294.1 [(M+H)$^+$], mp 247° C., was prepared in accordance with the general method of example 1 from 7-bromo-5-cyano-1H-indole-2-carboxamide (Intermediate 7) (66 mg, 250 mol) and commercially available 4-fluoro-3-methyl-phenylboronic acid (50.0 mg, 0.325 mmol).

EXAMPLE 67

5-Cyano-1-methyl-7-(4-nitrophenyl)-indole-2-carboxamide

The title compound, yellow solid (64 mg, 80%), MS (ISP) m/z=321.1 [(M+H)$^+$], mp 236° C., was prepared in accordance with the general method of example 1 from 7-bromo-5-cyano-1-methylindole-2-carboxamide (Intermediate 8) (69.5 mg, 250 µmol) and commercially available 4-nitro-phenylboronic acid (54.3 mg, 0.325 mmol).

EXAMPLE 68

5-Cyano-7-(4-nitrophenyl)-1H-indole-2-carboxamide

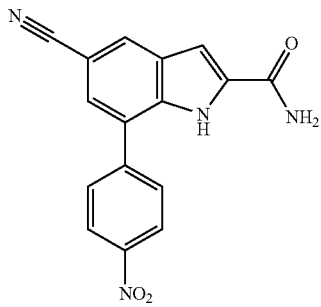 [SMILES: N#Cc1cc(-c2ccc([N+](=O)[O-])cc2)c2[nH]c(C(N)=O)cc2c1]

The title compound, yellow solid (30 mg, 39%), MS (ISP) m/z=307.1 [(M+H)⁺], mp 269° C., was prepared in accordance with the general method of example 1 from 7-bromo-5-cyano-1H-indole-2-carboxamide (Intermediate 7) (66 mg, 250 μmol) and commercially available 4-nitro-phenylboronic acid (54.3 mg, 0.325 mmol).

EXAMPLE 69

7-(2-Chloropyridin-4-yl)-5-cyano-1-methylindole-2-carboxamide

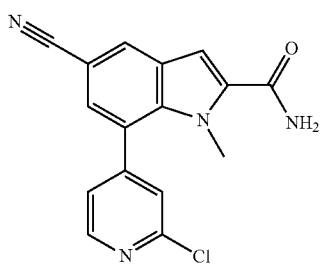

The title compound, off-white solid (46 mg, 59%), MS (ISP) m/z=311.1 [(M+H)⁺], mp 209° C., was prepared in accordance with the general method of example 1 from 7-bromo-5-cyano-1-methylindole-2-carboxamide (Intermediate 8) (69.5 mg, 250 μmol) and commercially available 2-chloro-pyridin-4-ylboronic acid (51.1 mg, 0.325 mmol).

EXAMPLE 70

7-(2-Chloropyridin-4-yl)-5-cyano-1H-indole-2-carboxamide

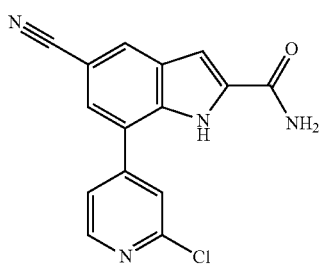 [SMILES: N#Cc1cc(-c2ccnc(Cl)c2)c2[nH]c(C(N)=O)cc2c1]

The title compound, light red solid (17 mg, 23%), MS (ISP) m/z=297.1 [(M+H)⁺], mp 297° C., was prepared in accordance with the general method of example 1 from 7-bromo-5-cyano-1H-indole-2-carboxamide (Intermediate 7) (66 mg, 250 mol) and commercially available 2-chloro-pyridin-4-ylboronic acid (51.1 mg, 0.325 mmol).

EXAMPLE 71

5-Cyano-7-(4-methoxyphenyl)-1-methylindole-2-carboxamide

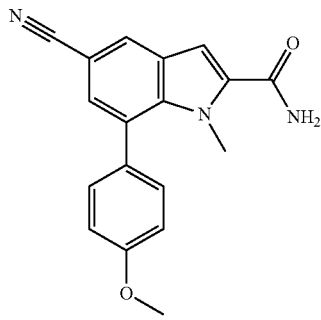 [SMILES: COc1ccc(-c2cc(C#N)cc3cc(C(N)=O)n(C)c23)cc1]

The title compound, off-white solid (61 mg, 80%), MS (ISP) m/z=306.1 [(M+H)⁺], mp 206.5° C., was prepared in accordance with the general method of example 1 from 7-bromo-5-cyano-1-methylindole-2-carboxamide (Intermediate 8) (69.5 mg, 250 mol) and commercially available 4-methoxy-phenylboronic acid (49.4 mg, 0.325 mmol).

EXAMPLE 72

5-Cyano-7-(4-methoxyphenyl)-1H-indole-2-carboxamide

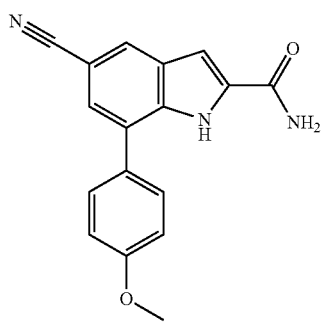 [SMILES: COc1ccc(-c2cc(C#N)cc3cc(C(N)=O)[nH]c23)cc1]

The title compound, light grey solid (49 mg, 67%), MS (ISP) m/z=292.1 [(M+H)⁺], mp 255° C., was prepared in accordance with the general method of example 1 from 7-bromo-5-cyano-1H-indole-2-carboxamide (Intermediate 7) (66 mg, 250 μmol) and commercially available 4-methoxy-phenylboronic acid (49.4 mg, 0.325 mmol).

EXAMPLE 73

5-Cyano-1-methyl-7-[4-(trifluoromethoxy)phenyl]indole-2-carboxamide

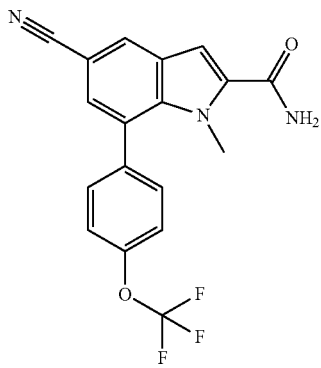 [SMILES: Cn1c(C(N)=O)cc2cc(C#N)cc(-c3ccc(OC(F)(F)F)cc3)c21]

The title compound, off-white solid (66 mg, 74%), MS (ISP) m/z=360.1 [(M+H)+], mp 176° C., was prepared in accordance with the general method of example 1 from 7-bromo-5-cyano-1-methylindole-2-carboxamide (Intermediate 8) (69.5 mg, 250 μmol) and commercially available 4-trifluoromethoxy-phenylboronic acid (66.9 mg, 0.325 mmol).

EXAMPLE 74

5-Fluoro-3-methyl-7-(4-methylphenyl)-1H-indole-2-carboxamide

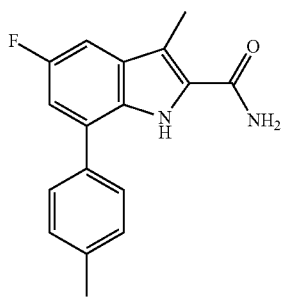 [SMILES: Cc1ccc(-c2cc(F)cc3c(C)c(C(N)=O)[nH]c23)cc1]

The title compound, off-white solid (52 mg, 74%), MS (ISP) m/z=283.1 [(M+H)+], mp 192° C., was prepared in accordance with the general method of example 1 from 7-bromo-5-fluoro-3-methyl-1H-indole-2-carboxamide (Intermediate 9) (67.8 mg, 250 mol) and commercially available p-tolylboronic acid (44.2 mg, 0.325 mmol).

EXAMPLE 75

5-Fluoro-3-methyl-7-(2,3,4-trifluorophenyl)-1H-indole-2-carboxamide

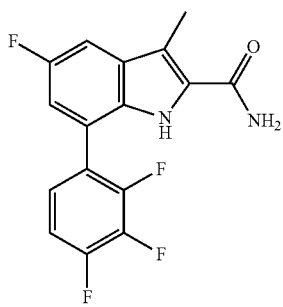 [SMILES: Cc1c(C(N)=O)[nH]c2c(-c3ccc(F)c(F)c3F)cc(F)cc12]

The title compound, white solid (19 mg, 24%), MS (ISP) m/z=323.1 [(M+H)+], mp 209° C., was prepared in accordance with the general method of example 1 from 7-bromo-5-fluoro-3-methyl-1H-indole-2-carboxamide (Intermediate 9) (67.8 mg, 250 μmol) and commercially available 2,3,4-trifluorophenylboronic acid (57.2 mg, 0.325 mmol).

EXAMPLE 76

5-Fluoro-7-(4-methoxyphenyl)-3-methyl-1H-indole-2-carboxamide

The title compound, white solid (47 mg, 63%), MS (ISP) m/z=299.1 [(M+H)+], mp 217° C., was prepared in accordance with the general method of example 1 from 7-bromo-5-fluoro-3-methyl-1H-indole-2-carboxamide (Intermediate 9) (67.8 mg, 250 μmol) and commercially available 4-methoxy-phenylboronic acid (49.4 mg, 0.325 mmol).

Example 77

7-(4-Chloro-2-fluorophenyl)-5-fluoro-3-methyl-1H-indole-2-carboxamide

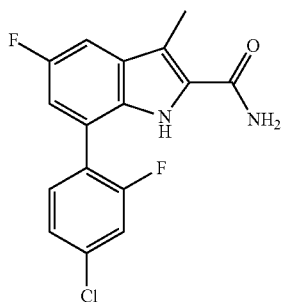 [SMILES: Cc1c(C(N)=O)[nH]c2c(-c3ccc(Cl)cc3F)cc(F)cc12]

The title compound, white solid (41 mg, 51%), MS (ISP) m/z=321.1 [(M+H)$^+$], mp 216° C., was prepared in accordance with the general method of example 1 from 7-bromo-5-fluoro-3-methyl-1H-indole-2-carboxamide (Intermediate 9) (67.8 mg, 250 µmol) and commercially available 4-chloro-2-fluoro-phenylboronic acid (56.7 mg, 0.325 mmol).

Example 78

5-Fluoro-3-methyl-7-pyridin-4-yl-1H-indole-2-carboxamide

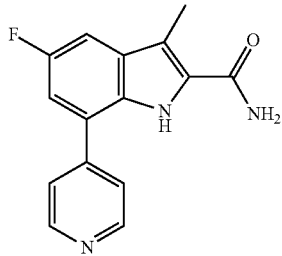 [SMILES: Cc1c(C(N)=O)[nH]c2c(-c3ccncc3)cc(F)cc12]

The title compound, light orange solid (29 mg, 43%), MS (ISP) m/z=270.2 [(M+H)$^+$], mp 270° C., was prepared in accordance with the general method of example 1 from 7-bromo-5-fluoro-3-methyl-1H-indole-2-carboxamide (Intermediate 9) (67.8 mg, 250 µmol) and commercially available pyridine-4-ylboronic acid (39.9 mg, 0.325 mmol).

We claim:
1. A compound of formula I

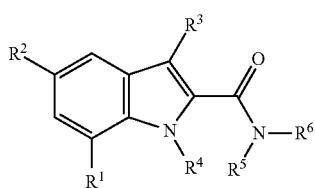

wherein
$R^1$ is aryl or heteroaryl, which are optionally substituted by one, two or three substituents, selected from lower alkyl, halogen, lower alkyl substituted by halogen, hydroxyl, lower alkoxy, lower alkoxy substituted by halogen, cyano or nitro;
$R^2$ is halogen, lower alkyl or cyano;
$R^3$ is hydrogen or lower alkyl;
$R^4$ is hydrogen or lower alkyl;
$R^5$, $R^6$ are independently hydrogen or lower alkyl, or $R^5$ and $R^6$ together with the N-atom to which they are attached form a heterocycloalkyl ring;
or a pharmaceutically acceptable acid addition salt, a racemic mixture or its corresponding enantiomer and/or optical isomers thereof.

2. The compound of formula I according to claim 1, wherein $R^1$ is aryl, which is optionally substituted by one, two or three substituents, selected from lower alkyl, halogen, lower alkyl substituted by halogen, hydroxyl, lower alkoxy, lower alkoxy substituted by halogen, cyano or nitro, and the other substituents are as described in claim 1.

3. The compound of formula I according to claim 2, wherein $R^1$ is phenyl, which is optionally substituted by one, two or three substituents, selected from lower alkyl, halogen, lower alkyl substituted by halogen, hydroxyl, lower alkoxy, lower alkoxy substituted by halogen, cyano or nitro.

4. The compound of formula I according to claim 1, which compounds are selected from the group consisting of:
7-(4-chlorophenyl)-5-cyano-1,3-dimethylindole-2-carboxamide;
5-fluoro-7-(4-fluorophenyl)-1-methylindole-2-carboxamide;
5-fluoro-7-(4-fluorophenyl)-1H-indole-2-carboxamide;
5-cyano-7-(4-fluorophenyl)-1,3-dimethylindole-2-carboxamide;
5-cyano-7-(3,4-difluorophenyl)-1,3-dimethylindole-2-carboxamide;
5-cyano-1,3-dimethyl-7-[4-(trifluoromethyl)-phenyl]-indole-2-carboxamide;
5-cyano-7-(3,4-difluorophenyl)-3-methyl-1H-indole-2-carboxamide;
5-Cyano-3-methyl-7-[4-(trifluoromethyl)phenyl]-1H-indole-2-carboxamide;
5-cyano-7-(4-fluorophenyl)-3-methyl-1H-indole-2-carboxamide;
7-(4-chlorophenyl)-5-cyano-3-methyl-1H-indole-2-carboxamide;
5-chloro-7-(4-fluorophenyl)-3-methyl-1H-indole-2-carboxamide;
5-chloro-7-(4-chlorophenyl)-3-methyl-1H-indole-2-carboxamide;
5-chloro-7-(4-fluorophenyl)-1,3-dimethylindole-2-carboxamide;
5-chloro-7-(4-chlorophenyl)-1,3-dimethylindole-2-carboxamide;
5-chloro-7-(3,4-difluorophenyl)-3-methyl-1H-indole-2-carboxamide;
5-chloro-3-methyl-7-[4-(trifluoromethyl)-phenyl]-1H-indole-2-carboxamide;
5-chloro-7-(3,4-difluorophenyl)-1,3-dimethylindole-2-carboxamide;
5-chloro-1,3-dimethyl-7-[4-(trifluoromethyl)phenyl]indole-2-carboxamide;
5-cyano-3-methyl-7-[4-(trifluoromethoxy)-phenyl]-1H-indole-2-carboxamide;
5-cyano-7-(4-cyanophenyl)-3-methyl-1H-indole-2-carboxamide;

5-cyano-1,3-dimethyl-7-[4-(trifluoromethoxy)phenyl]indole-2-carboxamide;
5-cyano-7-(4-cyanophenyl)-1,3-dimethylindole-2-carboxamide;
5-chloro-7-(4-cyanophenyl)-3-methyl-1H-indole-2-carboxamide;
5-chloro-3-methyl-7-[4-(trifluoromethoxy)phenyl]-1H-indole-2-carboxamide;
5-chloro-7-(2,4-difluorophenyl)-3-methyl-1H-indole-2-carboxamide;
5-chloro-7-(2,4-dichlorophenyl)-3-methyl-1H-indole-2-carboxamide;
5-chloro-1,3-dimethyl-7-[4-(trifluoromethoxy)-phenyl]indole-2-carboxamide;
5-chloro-7-(4-cyanophenyl)-1,3-dimethylindole-2-carboxamide;
5-chloro-7-(2,4-difluorophenyl)-1,3-dimethylindole-2-carboxamide;
5-chloro-7-(2,4-dichlorophenyl)-1,3-dimethylindole-2-carboxamide;
5-chloro-7-(4-chloro-3-fluorophenyl)-3-methyl-1H-indole-2-carboxamide;
5-chloro-7-(4-chloro-3-fluorophenyl)-1,3-dimethylindole-2-carboxamide;
5-cyano-7-(3,4-difluorophenyl)-1H-indole-2-carboxamide;
5-cyano-7-(4-fluorophenyl)-1H-indole-2-carboxamide;
7-(4-chlorophenyl)-5-cyano-1H-indole-2-carboxamide;
5-cyano-7-[4-(trifluoromethyl)phenyl]-1H-indole-2-carboxamide;
5-cyano-1-methyl-7-[4-(trifluoromethyl)-phenyl]-indole-2-carboxamide;
5-cyano-7-(4-fluorophenyl)-1-methylindole-2-carboxamide;
7-(4-chlorophenyl)-5-cyano-1-methylindole-2-carboxamide;
5-cyano-7-(3,4-difluorophenyl)-1-methylindole-2-carboxamide;
5-cyano-7-(2,4-difluorophenyl)-1H-indole-2-carboxamide;
5-cyano-7-(2,4-dichlorophenyl)-1H-indole-2-carboxamide;
5-cyano-7-(4-cyanophenyl)-1H-indole-2-carboxamide;
5-cyano-7-[4-(trifluoromethoxy)-phenyl]-1H-indole-2-carboxamide;
5-fluoro-7-(4-fluorophenyl)-3-methyl-1H-indole-2-carboxamide;
7-(4-chlorophenyl)-5-fluoro-3-methyl-1H-indole-2-carboxamide;
7-(3,4-difluorophenyl)-5-fluoro-3-methyl-1H-indole-2-carboxamide;
5-fluoro-3-methyl-7-[4-(trifluoromethyl)-phenyl]-1H-indole-2-carboxamide;
5-fluoro-7-(4-fluorophenyl)-1,3-dimethylindole-2-carboxamide;
7-(4-chlorophenyl)-5-fluoro-1,3-dimethylindole-2-carboxamide;
5-fluoro-1,3-dimethyl-7-[4-(trifluoromethyl)-phenyl]-indole-2-carboxamide;
7-(3,4-difluorophenyl)-5-fluoro-1,3-dimethylindole-2-carboxamide;
7-(4-cyanophenyl)-5-fluoro-3-methyl-1H-indole-2-carboxamide;
5-fluoro-3-methyl-7-[4-(trifluoromethoxy)phenyl]-1H-indole-2-carboxamide;
7-(2,4-difluorophenyl)-5-fluoro-3-methyl-1H-indole-2-carboxamide;
7-(2,4-dichlorophenyl)-5-fluoro-3-methyl-H-indole-2-carboxamide;
7-(4-chloro-2-fluorophenyl)-5-cyano-1H-indole-2-carboxamide;
7-(4-chloro-2-fluorophenyl)-5-cyano-1-methylindole-2-carboxamide;
7-(4-cyanophenyl)-5-fluoro-1,3-dimethylindole-2-carboxamide;
5-fluoro-1,3-dimethyl-7-[4-(trifluoromethoxy)phenyl]indole-2-carboxamide;
7-(2,4-dichlorophenyl)-5-fluoro-1,3-dimethylindole-2-carboxamide;
5-cyano-7-(2,4-difluorophenyl)-1-methylindole-2-carboxamide;
5-cyano-7-(2,4-dichlorophenyl)-1-methylindole-2-carboxamide;
7-(2,4-difluorophenyl)-5-fluoro-1,3-dimethylindole-2-carboxamide;
5-cyano-7-(4-fluoro-3-methylphenyl)-1-methylindole-2-carboxamide;
5-cyano-7-(4-fluoro-3-methylphenyl)-1H-indole-2-carboxamide;
5-cyano-1-methyl-7-(4-nitrophenyl)-indole-2-carboxamide;
5-cyano-7-(4-nitrophenyl)-1H-indole-2-carboxamide;
5-cyano-7-(4-methoxyphenyl)-1-methylindole-2-carboxamide;
5-cyano-7-(4-methoxyphenyl)-1H-indole-2-carboxamide;
5-cyano-1-methyl-7-[4-(trifluoromethoxy)phenyl]indole-2-carboxamide;
5-fluoro-3-methyl-7-(4-methylphenyl)-1H-indole-2-carboxamide;
5-fluoro-3-methyl-7-(2,3,4-trifluorophenyl)-1H-indole-2-carboxamide;
5-fluoro-7-(4-methoxyphenyl)-3-methyl-1H-indole-2-carboxamide;
7-(4-chloro-2-fluorophenyl)-5-fluoro-3-methyl-1H-indole-2-carboxamide; and,
5-fluoro-3-methyl-7-pyridin-4-yl-1H-indole-2-carboxamide; or,
a pharmaceutically acceptable acid addition salt, a racemic mixture or its corresponding enantiomer and/or optical isomers thereof.

5. The compound of formula I according to claim 1, wherein $R^1$ is heteroaryl, which is optionally substituted by one, two or three substituents, selected from lower alkyl, halogen, lower alkyl substituted by halogen, hydroxyl, lower alkoxy, lower alkoxy substituted by halogen, cyano or nitro and the other substituents are as described in claim 1.

6. The compound of formula I according to claim 5, wherein $R^1$ is pyridyl, which is optionally substituted by one, two or three substituents, selected from lower alkyl, halogen, lower alkyl substituted by halogen, hydroxyl, lower alkoxy, lower alkoxy substituted by halogen, cyano or nitro.

7. The compound of formula I according to claim 6, which compounds are selected from the group consisting of:
7-(2-chloropyridin-4-yl)-5-cyano-1-methylindole-2-carboxamide;
7-(2-chloropyridin-4-yl)-5-cyano-1H-indole-2-carboxamide; and,
5-fluoro-3-methyl-7-pyridin-4-yl-1H-indole-2-carboxamide; or,
a pharmaceutically acceptable acid addition salt, a racemic mixture or its corresponding enantiomer and/or optical isomers thereof.

8. A process for the manufacture of a compound of formula I wherein
R¹ is aryl or heteroaryl, which are optionally substituted by one, two or three substituents, selected from lower alkyl, halogen, lower alkyl substituted by halogen, hydroxyl, lower alkoxy, lower alkoxy substituted by halogen, cyano or nitro;
R² is halogen, lower alkyl or cyano;
R³ is hydrogen or lower alkyl;
R⁴ is hydrogen or lower alkyl;
R⁵, R⁶ are independently hydrogen or lower alkyl, or R⁵ and R⁶ together with the N-atom to which they are attached form a heterocycloalkyl ring;
which process comprises the steps of:
a) reacting a compound of formula II wherein X is halo or —OH

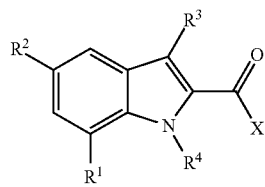

(II)

with a compound of formula III
NHR⁵R⁶    (III)
to afford a compound of formula I

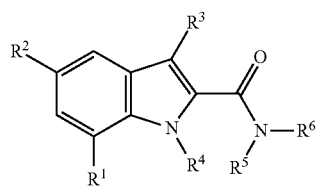

I and, optionally, converting the compounds obtained into pharmaceutically acceptable acid addition salts.

9. A process for the manufacture of a compound of formula I wherein
R¹ is aryl or heteroaryl, which are optionally substituted by one, two or three substituents, selected from lower alkyl, halogen, lower alkyl substituted by halogen, hydroxyl, lower alkoxy, lower alkoxy substituted by halogen, cyano or nitro;
R² is halogen, lower alkyl or cyano;
R³ is hydrogen or lower alkyl;
R⁴ is hydrogen or lower alkyl;
R⁵, R⁶ are independently hydrogen or lower alkyl, or R⁵ and R⁶ together with the N-atom to which they are attached form a heterocycloalkyl ring;

which process comprises the steps of:
a) reacting a compound of formula IV

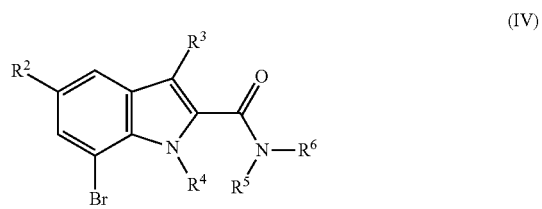

(IV)

with a compound of formula V

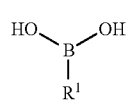

(V)

to afford a compound of formula I

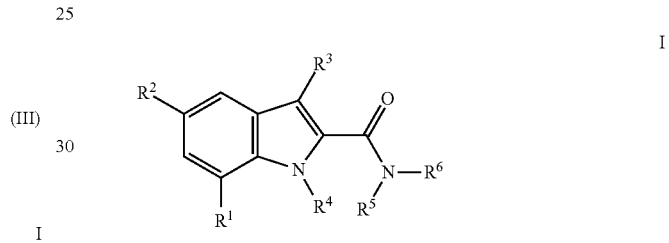

I and, optionally, converting the compounds obtained into pharmaceutically acceptable acid addition salts.

10. A pharmaceutical composition comprising a compound of claim 1 and at least one pharmaceutically acceptable excipient, carrier or diluent.

11. A method for the treatment of schizophrenia, obsessive-compulsive personality disorder, depression, bipolar disorders, anxiety disorders, epilepsy, retinal degeneration, traumatic brain injury, spinal cord injury, post-traumatic stress disorder, panic disorder, Parkinson's disease, dementia, Alzheimer's disease, cognitive impairment, chemotherapy-induced cognitive dysfunction, Down syndrome, autism spectrum disorders, hearing loss, tinnitus, spinocerebellar ataxia, amyotrophic lateral sclerosis, multiple sclerosis, Huntington's disease, stroke, radiation therapy, chronic stress, abuse of neuro-active drugs, selected from alcohol, opiates, methamphetamine, phencyclidine and cocaine, comprising administering to a patient in need thereof a therapeutically effective amount of a compound of claim 1.

* * * * *